US006572980B1

(12) United States Patent
Klemarczyk et al.

(10) Patent No.: US 6,572,980 B1
(45) Date of Patent: Jun. 3, 2003

(54) REWORKABLE THERMOSETTING RESIN COMPOSITIONS

(75) Inventors: Philip T. Klemarczyk, Canton, CT (US); Andrew D. Messana, Newington, CT (US)

(73) Assignee: Henkel Loctite Corporation, Rocky Hill, CT (US)

( * ) Notice: Subject to any disclaimer, the term of this patent is extended or adjusted under 35 U.S.C. 154(b) by 0 days.

(21) Appl. No.: 10/113,578

(22) Filed: Apr. 2, 2002

Related U.S. Application Data

(60) Provisional application No. 60/311,347, filed on Aug. 13, 2001.

(51) Int. Cl.$^7$ ................................................ H01L 29/12
(52) U.S. Cl. ...................... 428/620; 257/787; 257/788; 257/793; 528/380; 528/417; 528/421; 549/1; 549/90; 549/546; 549/554; 549/555; 549/562
(58) Field of Search ................................. 257/787, 788, 257/793; 428/620; 528/380, 417, 421; 549/1, 90, 546, 554, 555, 562

(56) References Cited

U.S. PATENT DOCUMENTS

| | | | |
|---|---|---|---|
| 4,756,989 A | * | 7/1988 | Ai et al. ..................... 430/272 |
| 5,355,580 A | | 10/1994 | Tsukada ....................... 29/840 |
| 5,512,613 A | | 4/1996 | Afzali-Ardakani et al. . 523/443 |
| 5,560,934 A | | 10/1996 | Afzali-Ardakani et al. . 424/497 |
| 5,760,337 A | | 6/1998 | Iyer et al. ................... 174/52.2 |
| 5,783,867 A | | 7/1998 | Belke, Jr. et al. ........... 257/783 |
| 5,872,158 A | | 2/1999 | Kuczynski ................... 522/182 |
| 5,932,682 A | | 8/1999 | Buchwalter et al. .......... 528/94 |
| 5,948,922 A | | 9/1999 | Ober et al. .................. 549/547 |
| 5,973,033 A | | 10/1999 | Ober et al. .................. 523/443 |

FOREIGN PATENT DOCUMENTS

| | | | |
|---|---|---|---|
| JP | 69280/94 | 8/1992 | ............ H01L/21/60 |
| JP | 102343/93 | 4/1993 | ............ H01L/23/15 |
| JP | 251516/93 | 6/1993 | ............ H01L/21/60 |
| JP | 77264/94 | 3/1994 | ............ H01L/21/52 |
| WO | PCT/US98/00858 | 7/1998 | ............ C08K/5/09 |

OTHER PUBLICATIONS

Chemical Abstract Registration No. 15817–14–8.

\* cited by examiner

*Primary Examiner*—Robert Dawson
*Assistant Examiner*—D. Aylward
(74) *Attorney, Agent, or Firm*—Steven C. Bauman

(57) ABSTRACT

This invention relates to thermosetting resin compositions useful for mounting onto a circuit board semiconductor devices, such as CSPs, BGAs, LGAs and the like, each of which having a semiconductor chip, such as LSI, on a carrier substrate. The compositions of this invention are reworkable when subjected to appropriate conditions.

31 Claims, 7 Drawing Sheets

FIG. 2 Reworkable Underfill Process Flow

REWORKABLE THERMOSETTING RESIN COMPOSITIONS

This application claims benefit of provisional application Ser. No. 60/311,347 filed Aug. 13, 2001.

BACKGROUND OF THE INVENTION

1. Field of the Invention

This invention relates to thermosetting resin compositions useful for mounting onto circuit board semiconductor devices, such as chip size or chip scale packages ("CSPs"), ball grid arrays ("BGAs"), land grid arrays ("LGAs") and the like, each of which having a semiconductor chip, such as large scale integration ("LSI"), on a carrier substrate. The compositions of this invention are reworkable when subjected to appropriate conditions.

2. Brief Description of Related Technology

In recent years, the popularity of small-sized electronic appliances, such as camera-integrated video tape recorders ("VTRs") and portable telephone sets, has made size reduction of LSI devices desirable. As a result, CSPs, BGAs and LGAs are being used to reduce the size of packages substantially to that of bare chips. Such CSPs, BGAs and LGAs improve the characteristics of the electronic device while retaining many of their operating features, thus serving to protect semiconductor bare chips, such as LSIs, and facilitate testing thereof.

Ordinarily, the CSP/BGA/LGA assembly is connected to electrical conductors on a circuit board by use of a solder connection or the like. However, when the resulting CSP/BGA/LGA circuit board structure is exposed to thermal cycling, the reliability of the solder connection between the circuit board and the CSP/BGA/LGA often becomes suspect. Recently, after a CSP/BGA/LGA assembly is mounted on a circuit board, the space between the CSP/BGA/LGA assembly and the circuit board is often now filled with a sealing resin (often referred to as underfill sealing) in order to relieve stresses-caused by thermal cycling, thereby improving heat shock properties and enhancing the reliability of the structure.

However, since thermosetting resins are typically used as the underfill sealing material, in the event of a failure after the CSP/BGA/LGA assembly is mounted on the circuit board, it is very difficult to replace the CSP/BGA/LGA assembly without destroying or scrapping the structure in its entirety.

To that end, techniques for mounting a bare chip on a circuit board are accepted as substantially similar to the mounting of a CSP/BGA/LGA assembly onto a circuit board. One such technique, disclosed in Japanese Laid-Open Patent Publication No. 102343/93, involves a mounting process where a bare chip is fixed and connected to a circuit board by use of a photocurable adhesive, where, in the event of failure, this bare chip is removed therefrom. However, this technique is limited to those instances where the circuit board includes a transparent substrate (e.g., glass) which permits exposure to light from the back side, and the resulting structure exhibits poor heat shock properties.

Japanese Laid-Open Patent Publication No. 69280/94 discloses a process where a bare chip is fixed and connected to a substrate by use of a resin capable of hardening at a predetermined temperature. In the event of failure, this bare chip is removed from the substrate by softening the resin at a temperature higher than the predetermined temperature. However, no specific resin is disclosed, and there is no disclosure about treating the resin which remains on the substrate. Thus, the disclosed process is at best incomplete.

As pointed out in Japanese Laid-Open Patent Publication No. 77264/94, it is conventional to use a solvent to remove residual resin from a circuit board. However, swelling the resin with a solvent is a time consuming process and the corrosive organic acid ordinarily used as the solvent may reduce the reliability of the circuit board. Instead, that disclosure speaks to a method for removing residual resin by irradiation with electromagnetic radiation.

Japanese Laid-Open Patent Publication No. 251516/93 also discloses a mounting process using bisphenol A type epoxy resin (CV5183 or CV5183S; manufactured by Matsushita Electric Industrial Co., Ltd.). However, the removal process so disclosed does not consistently permit easy removal of the chip, the curing step is lengthy at elevated temperatures, and the process generally results in poor productivity.

Of course, mechanical methods of removing/replacing semiconductor chips from/on a substrate are known, such as by cutting the chip to be removed/replaced. See U.S. Pat. No. 5,355,580 (Tsukada).

Thermoplastic underfill resins are known for use in semiconductor chip attachment. See U.S. Pat. No. 5,783,867 (Belke, Jr.). However, such thermoplastic resins tend to leak under relatively modest temperature conditions. In contrast, thermosetting resins cure into a matrix which ordinarily have greater thermal stability under end use operating temperatures.

U.S. Pat. No. 5,512,613 (Afzali-Ardakani), U.S. Pat. No. 5,560,934 (Afzali-Ardakani) and U.S. Pat. No. 5,932,682 (Buchwalter), each refer to a reworkable thermoset composition based on a diepoxide component in which the organic linking moiety connecting the two epoxy groups of the diepoxide includes an acid cleavable acyclic acetal group. With such acid cleavable acyclic acetal groups forming the bases of the reworkable composition, a cured thermoset need only be introduced to an acidic environment in order to achieve softening and a loss of much of its adhesiveness.

U.S. Pat. No. 5,872,158 (Kuczynski) refers to thermosetting compositions capable of curing upon exposure to actinic radiation, which are based on acetal diacrylates, and reaction products of which are reported to be soluble in dilute acid.

U.S. Pat. No. 5,760,337 (Iyer) refers to thermally reworkable crosslinked resins to fill the gap created between a semiconductor device and a substrate to which it is attached. These resins are produced by reacting a dienophile (with a functionality greater than 1) with a 2.5-dialkyl substituted furan-containing polymer.

International Patent Publication No. PCT/US98/00858 refers to a thermosetting resin composition capable of sealing underfilling between a semiconductor device including a semiconductor chip mounted on a carrier substrate and a circuit board to which said semiconductor device is electrically connected. The composition includes about 100 parts by weight of an epoxy resin, about 3 to about 60 parts by weight of a curing agent, and about 1 to about 90 parts by weight of a plasticizer. Here, the area around the cured thermoset is to be heated at a temperature of about 190 to about 260° C. for a period of time ranging from about 10 seconds to about 1 minute in order to achieve softening and a loss of much of its adhesiveness.

U.S. Pat. No. 5,948,922 (Ober) and U.S. Pat. No. 5,973,033 (Ober), each refer to a certain class of compounds having tertiary oxycarbonyl linkages, and compositions based on such compounds, which when cured provide thermally decomposable compositions capable of being reworked.

Recent commercial interest has led to industry efforts to produce underfill sealants based on other curable resins which are capable of being reworked, particularly where the underfill sealants have been designed to withstand subsequent solder reflow cycles. To date, it is believed that such an underfill sealant has not been described.

Accordingly, it would be desirable for an underfilling sealing material to provide good productivity, while allowing the substrates with which it is to be used to be readily processed and easily separated from a semiconductor device without application of acidic media, or extreme elevated temperature conditions that may compromise the integrity of the semiconductor devices remaining on the substrate or the substrate itself, but where temperature conditions are greater than those employed in the past.

SUMMARY OF THE INVENTION

The present invention provides a thermosetting resin composition, which includes broadly a curable resin component, at least a portion of which is an epoxy- or episulfide-containing aromatic compound; an optional inorganic filler component; and a curing agent component including an anhydride component, a nitrogen-containing component, such as an aza compound, amine compound, an amide compound, and/or an imidazole compound, and combinations thereof.

The epoxy- or episulfide-containing aromatic compounds are within the following formula:

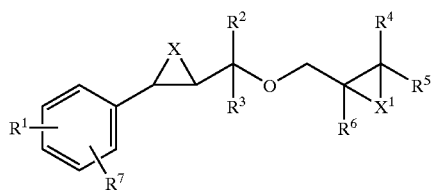

I where $R^1$ and $R^7$ are each independently selected from hydrogen, methyl, ethyl, propyl, isopropyl, butyl, isobutyl, t-butyl, $C_{1-4}$ alkoxy, halogen, cyano and nitro, and $R^2$ through $R^6$ may or may not independently be present, but when present are each independently selected from hydrogen methyl, ethyl, propyls, and butyls, and aryl, such as phenyl, benzyl, phenoxyl, benzyloxy and derivatives thereof, such as alkyl derivatives, and when $R^5$ and $R^6$ are present, and taken together, may form a cyclic or bicyclic structure, such as a carbocyclic (e.g., cyclopropyl, cyclobutyl, cyclopentyl, cyclohexyl, cycloheptyl, or norbornyl) or a heterocyclic structure, which cyclic structures may be substituted by straight chain or branched alkyl groups of from 1 to about 6 carbon atoms, or straight chain or branched alkenyl groups of from 2 to about 6 carbon atoms, and X and $X_1$ are each independently selected from oxygen and sulfur.

Particularly desirable epoxy- or episulfide-containing aromatic compounds within formula I are given in the section entitled "Detailed Description of the Invention" under formulae II or III, respectively, which follows hereinafter.

Reaction products of these compositions are capable of softening under exposure to elevated temperature conditions, such as in excess of the tempertures used to cure the composition. Such temperature exposure combined with the epoxy compound having at least one thermally cleavable linkage provides the reworkable aspect of this invention. The remaining components, discussed below, provide the physical properties and characteristics for the compositions and reaction products to render the compositions attractive for commercial use, particularly in the microelectronics industry. To that end, the inventive thermosetting resin composition is useful as an underfilling sealing resin, and enables a semiconductor device, such as a CSP/BGA/LGA assembly which includes a semiconductor chip mounted on a carrier substrate, to be securely connected to a circuit board by short-time heat curing and with good productivity. Reaction products of the inventive compositions permit the semiconductor device to be easily removed from the circuit board by localized heating in the event of semiconductor device or connection failure. This makes it possible to reuse the circuit board (with the remaining functioning semiconductor devices still electrically attached) and thereby achieve an improvement in the yield of the production process and a reduction in production cost.

The compositions of this invention may also be used for microelectronic applications beyond sealing underfill, such as with glob top, direct chip attachment and other applications for thermosetting compositions.

In addition, the compositions may be used in far-flung applications, where thermosetting epoxies, or for that matter other thermosetting or thermoplastic adhesive, coating and sealant compositions, may be used. For instance, the compositions may be used in the assembly of products, whose component parts have value as do the intermediate/finished products, to facilitate assembly and disassembly thereof where defective component parts are found. In that event, the defective component part(s) may be readily removed from the intermediate/finished product(s) and be replaced without having to scrap the entire intermediate/finished product(s). In addition, the speed with which the disassembly may proceed allows throughput to remain high. A non-microelectronic example of such a part is the assembly of prosthetic devices.

The present invention also provides novel monomers within structure I.

Other benefits and advantages of the present invention will become more readily apparent after a reading of the "Detailed Description" section together with the figures.

DETAILED DESCRIPTION OF THE INVENTION

Figure 1:
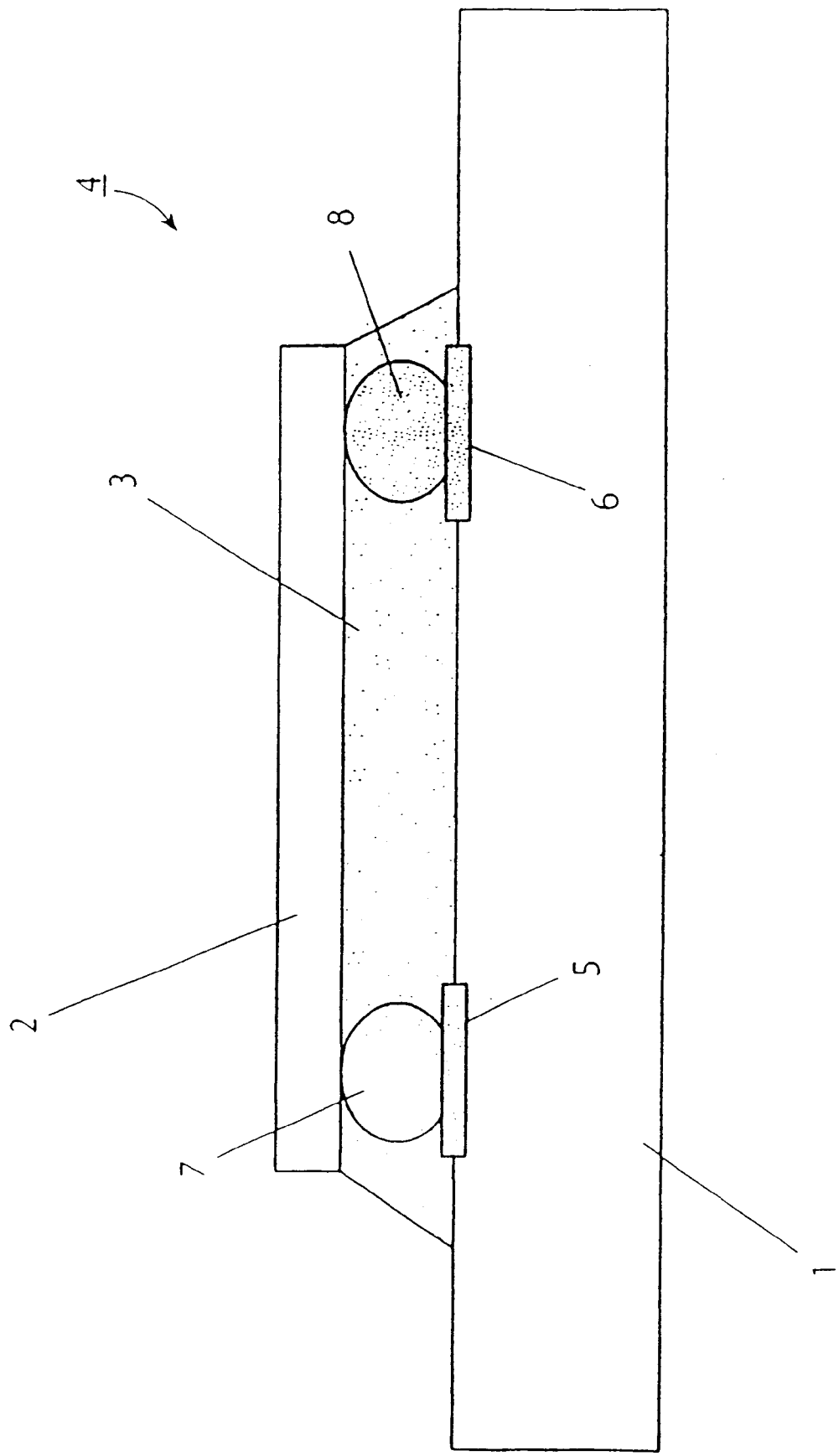
FIG. 1 depicts a cross-sectional view showing an example of the mounting structure in which the thermosetting resin composition of the present invention is used.

As noted above, the thermosetting resin compositions which are useful as underfill sealants between a semiconductor device and a circuit board to which the semiconductor device is electrically connected or a semiconductor chip and a circuit board to which the semiconductor chip is electrically connected, includes broadly (a) a curable resin component, at least a portion of which is an epoxy- or episulfide-containing aromatic compound, and (b) a curing agent component selected from an anhydride component, a nitrogen-containing component, such as an amine compound, an amide compound, and/or an imidazole compound, and combinations thereof. Reaction products of these compositions are capable of softening under exposure to elevated temperature conditions, such as in excess of the temperature chosen to cure the composition. Loss of adhesion to the substrate occurs at temperatures greater than that which was used to cure the composition. For instance, at least about 50% of adhesion to the substrate is typically lost at temperatures in excess of about 200° C.

Typically, the composition includes about 10 to about 70 weight percent of the curable resin component by weight of the total composition, of which about 10 to about 75 weight percent thereof is comprised of an epoxy- or an episulfide-containing aromatic compound within structure I; and 3 to about 100 weight percent of the curing agent component, based on the total weight of the curable resin component, depending of course on the type and identity of the curing agent chosen. In addition, 0 to about 70 weight percent of an inorganic filler component and/or 0 to about 5 weight percent of a flowability agent may also be included.

Of course, depending on the particular set of properties desirable for a composition destined for a specific purpose these values may vary somewhat. Such variation may be achieved without undue experimentation by those persons skilled in the art, and accordingly are contemplated within the scope of the present invention.

The curable resin component of the present invention may include any common epoxy resin, such as a multifunctional epoxy resin. Ordinarily, the multifunctional epoxy resin should be included in an amount within the range of about 30 to about 70 weight percent, such as about 40 to about 60 weight percent, based on the weight of the total of the epoxy resin component. In the case of bisphenol-F-type epoxy resin, desirably the amount thereof should be in the range of from about 35 to about 65 weight percent, such as about 40 to about 50 weight percent of the total of the epoxy resin component.

Examples of the multifunctional epoxy resin include bisphenol-A-type epoxy resin, bisphenol-F-type epoxy resin (such as RE-404-S from Nippon Kayaku, Japan), phenol novolac-type epoxy resin, and cresol novolac-type epoxy from resin (such as "ARALDITE" ECN 1871 from Ciba Specialty Chemicals, Hawthorne, N.Y.).

Other suitable epoxy resins include polyepoxy compounds based on aromatic amines and epichlorohydrin, such as N,N,N',N'-tetraglycidyl-4,4'-diaminodiphenyl methane; N-diglycidyl-4-aminophenyl glycidyl ether; and N,N,N',N'-tetraglycidyl-1,3-propylene bis-4-aminobenzoate.

Among the epoxy resins suitable for use herein also include polyglycidyl derivatives of phenolic compounds, such as those available commercially under the tradename "EPON", such as "EPON" 828, "EPON" 1001, "EPON" 1009, and "EPON" 1031 from Shell Chemical Co.; "DER" 331, "DER" 332, "DER" 334, and "DER" 542 from Dow Chemical Co.; and "BREN-S" from Nippon Kayaku. Other suitable epoxy resins include polyepoxides prepared from polyols and the like and polyglycidyl derivatives of phenol-formaldehyde novolacs, the latter of which are available commercially under the tradename "DEN", such as "DEN" 431, "DEN" 438, and "DEN" 439 from Dow Chemical. Cresol analogs are also available commercially under the tradename "ARALDITE", such as "ARALDITE" ECN 1235, "ARALDITE" ECN 1273, and "ARALDITE" ECN 1299 from Ciba Specialty Chemicals. SU-8 is a bisphenol-A-type epoxy novolac available from Interez, Inc. Polyglycidyl adducts of amines, aminoalcohols and polycarboxylic acids are also useful in this invention, commercially available resins of which include "GLYAMINE" 135, "GLYAMINE" 125, and "GLYAMINE" 115 from F.I.C. Corporation; "ARALDITE" MY-720, "ARALDITE" 0500, and "ARALDITE" 0510 from Ciba Specialty Chemicals and PGA-X and PGA-C from the Sherwin-Williams Co.

And of course combinations of the different epoxy resins are also desirable for use herein.

The epoxy- or episulfide-containing aromatic compounds are within the following formula:

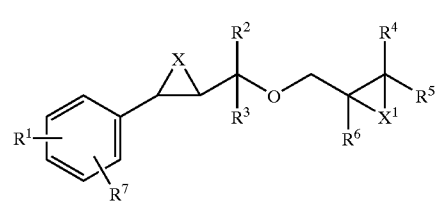

I where $R^1$ and $R^7$ are each independently selected from hydrogen, methyl, ethyl, propyl, isopropyl, butyl, isobutyl, t-butyl, $C_{1-4}$ alkoxy, halogen, cyano and nitro, and $R^2$ through $R^6$ may or may not independently be present, but when present are each independently selected from hydrogen, methyl, ethyl, propyls, and butyls, and aryl, such as phenyl, benzyl, phenoxyl, benzyloxy and derivatives thereof, and when $R_5$ and $R^6$ are present, and taken together, may form a cyclic or bicyclic structure, such as a carbocyclic (e.g., cyclopentyl, cyclohexyl, cycloheptyl or norbornyl) or a heterocyclic, which cyclic structures may be the same or different and may be substituted by straight chain or branched alkyl groups of from 1 to about 6 carbon atoms, and X and $X^1$ are each independently selected from oxygen and sulfur.

The epoxy-containing aromatic compounds are within the following formula:

II where $R^1$ and $R^7$ are each independently selected from hydrogen, methyl, ethyl, propyl, isopropyl, butyl, isobutyl, t-butyl, $C_{1-4}$ alkoxy, halogen, cyano and nitro, and $R^2$ through $R^6$ may or may not independently be present, but when present are each independently selected from hydrogen, methyl, ethyl, propyls, and butyls, and aryl, such as phenyl, benzyl, phenoxyl, benzyloxy and derivatives thereof, and when $R^5$ and $R^6$ are present, and taken together, may form a cyclic or bicyclic structure, such as a carbocyclic (e.g, cyclopentyl, cyclohexyl, cycloheptyl or norbornyl) or a heterocyclic, which cyclic structures may be the same or different and may be substituted by straight chain or branched alkyl groups of from 1 to about 6 carbon atoms.

Particularly desirable epoxy-containing aromatic compounds within formula II include:

Cinnamyl Oxide Glycidyl Ether (COGE)

Cinnamyl Oxide Methyl Propenyl Oxide Ether (COMPOE)

Cinnamyl Oxide Methyl Butene Oxide Ether (COMBOE)

di-Cinnamyl Oxide Ether (di-COE

The episulfide-containing aromatic compounds are within the following formula III:

III where $R^1$ and $R^7$ are each independently selected from hydrogen, methyl, ethyl, propyl, isopropyl, butyl, isobutyl, t-butyl, $C_{1-4}$ alkoxy, halogen, cyano and nitro, and $R^2$ through $R^6$ may or may not independently be present, but when present are each independently selected from hydrogen, methyl, ethyl, propyls, and butyls, and aryl, such as phenyl, benzyl, phenoxyl, benzyloxy and derivatives thereof, and when $R^5$ and $R^6$ are present, and taken together, may form a cyclic or bicyclic structure, such as a carbocyclic (e.g., cyclopentyl, cyclohexyl, cycloheptyl or norbornyl) or a heterocyclic, which cyclic structures may be the same or different and may be substituted by straight chain or branched alkyl groups of from 1 to about 6 carbon atoms.

Particularly desirable episulfide-containing aromatic compounds within formula III include:

Cinnamyl Episulfide Thioglycidyl Ether

Cinnamyl Episulfide Methyl Propenyl Episulfide Ether

Cinnamyl Episulfide Methyl Butene Episulfide Ether di-Cinnamyl Episulfide Ether

Particularly desirable mixed epoxy- and episulfide-containing aromatic compounds within formula I include:

Cinnamyl Oxide Thioglycidyl Ether

-continued

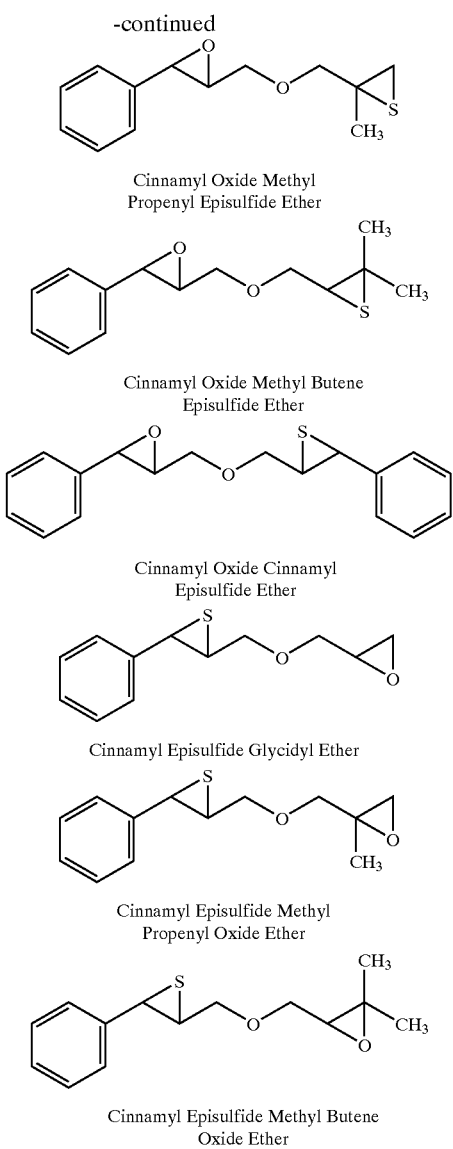

Cinnamyl Oxide Methyl
Propenyl Episulfide Ether

Cinnamyl Oxide Methyl Butene
Episulfide Ether

Cinnamyl Oxide Cinnamyl
Episulfide Ether

Cinnamyl Episulfide Glycidyl Ether

Cinnamyl Episulfide Methyl
Propenyl Oxide Ether

Cinnamyl Episulfide Methyl Butene
Oxide Ether

The presence in the curable resin component of the epoxy- or episulfide-containing aromatic compound(s) allows for repair, replacement, recovery and/or recycling of operative electronic components from assemblies that have become at least in part inoperative.

The epoxy compounds within structure I can be prepared along the lines described in the Examples section. In order to prepare the episulfide versions of those epoxy compounds, either as partial or full episulfides, see U.S. Pat. No. 3,378,522 (Martin) for conventional synthetic methods for preparing an episulfide from an epoxy. The reaction products of these synthetics oftentimes may be a statistical mixture of a diepoxide, a monoepoxide/monoepisulfide, and a diepisulfide.

As an inorganic filler component, many materials are potentially useful. For instance, the inorganic filler component may often include reinforcing silicas, such as fused silicas, and may be untreated or treated so as to alter the chemical nature of their surface. Virtually any reinforcing fused silica may be used.

Particularly desirable ones have a low ion concentration and are relatively small in particle size (e.g., in the range of about 2–10 microns, such as on the order of about 2 microns), such as the silica commercially available from Admatechs, Japan under the trade designation SO-E5.

Other desirable materials for use as the inorganic filler component include those constructed of or containing aluminum oxide, silicon nitride, aluminum nitride, silica-coated aluminum nitride, boron nitride and combinations thereof.

When used, the inorganic filler component should be used in an amount of about 10 to about 70 percent by weight of the compostion, such as about 25 to about 60 percent by weight, desirably within the range of about 35 to about 55 percent by weight.

The curing agent component should include materials capable of catalyzing the polymerization of the epoxy resin component of the inventive compositions. Desirable curing agents for use with the present invention include an anhydride component, a nitrogen-containing component, such as an aza compound, an amine compound, an amide compound, and an imidazole compound, and combinations thereof.

Appropriate anhydride compounds for use herein include mono- and poly-anhydrides, such as hexahydrophthalic anhydride ("HHPA") and methyl hexahydrophthalic anhydride ("MHHPA") (commercially available from Lindau Chemicals, Inc., Columbia, S.C., used individually or as a combination, which combination is available under the trade designation "LINDRIDE" 62C), 5-(2,5-dioxotetrahydrol)-3-methyl-3-cyclohexene-1,2-dicarboxylic anhydride (commercially available from ChrisKev Co., Leewood, Kans. under the trade designation B-4400) and nadic methyl anhydride.

Of course, combinations of these anhydryde compounds are also desirable for use in the compositions of the present invention.

The nitrogen-containing compounds include aza compounds (such as di-aza compounds or tri-aza compounds), examples of which include:

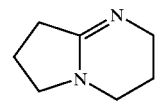

1, 5-Diazabicyclo [4.3.0] non-5-ene

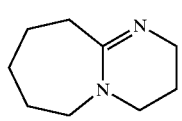

1, 8-Diazabicylco [5.4.0] undec-5-ene (DBU

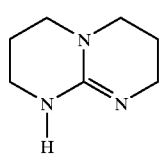

1, 5, 7-Triazabicyclo [4.4.0] dec-5-ene and the bicyclo mono- and di-aza compounds:

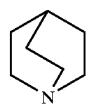

Quinuclidine

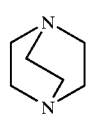

1, 4-Diazabicyclo [2.2.2] octane

Examples of the amine compounds include aliphatic polyamines, such as diethylenetriamine, triethylenetetramine and diethylaminopropylamine; aromatic polyamines, such as m-xylenediamine and diaminodiphenylamine; and alicyclic polyamines, such as isophoronediamine and menthenediamine.

Of course, combinations of these amine compounds are also desirable for use in the compositions of the present invention.

Examples of amide compounds include cyano-functionalized amides, such as dicyandiamide.

The imidazole compounds may be chosen from imidazole, isoimidazole, and substituted imidazoles—such as alkyl-substituted imidazoles (e.g., 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-1-cyanoethyl-2-undecylimidazole, 1-cyanoethyl-2-phenylimidazole, 1-guanaminoethyl-2-methylimidazole and addition products of an imidazole and trimellitic acid, 2-n-heptadecyl-4-methylimidazole and the like, generally where each alkyl substituent contains up to about 17 carbon atoms and desirably up to about 6 carbon atoms), and aryl-substituted imidazoles [e.g., phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4,2-naphthyl-4,5-diphenylimidazole, 1-benzyl-2-methylimidazole, 2-p-methoxystyrylimidazole, and the like, generally where each aryl substituent contains up to about 10 carbon atoms and desirably up to about 8 carbon atoms].

Examples of commercial imidazole compounds are available from Air Products, Allentown, Pa. under the trade designation "CUREZOL" 1B2MZ and from Synthron, Inc., Morganton, N.C. under the trade designation "ACTIRON" NXJ-60.

Examples of the modified imidazole compounds include imidazole adducts formed by the addition of an imidazole compound to an epoxy compound. For instance, "AJICURE" PN-23, commercially available from Ajinomoto Co., Inc., Tokyo, Japan, is believed to be an adduct of EPON 828 (bisphenol-A-type epoxy resin, epoxy equivalent 184-194, commercially available from Shell Chemical Co.), 2-ethyl-4-methylimidazole and phthalic anhydride. Others commercially available ones from Ajinomoto include "AMICURE" MY-24, "AMICURE" GG-216 and "AMICURE" ATU CARBAMATE. In addition, "NOVACURE" HX-3722 (an imidazole/bisphenol A epoxy adduct dispersed in bisphenol A epoxy) and "NOVACURE" HX-3921 HP, commercially available from Asahi-Ciba, Ltd., may also be used.

Of course, combinations of these imidazole compounds are also desirable for use in the compositions of the present invention.

The curing agent component may be used in an amount of from about 3 to about 100 weight percent, based on the weight of the curable aromatic resin component, depending of course on the type and identity of the curing agent component.

In addition, the composition may also include a flowability agent, such as a silane and/or titanate.

Appropriate silanes for use herein include octyl trimethoxy silane (commercially available from OSI Specialties Co., Danbury, Conn. under the trade designation A-137), and methacryloxy propyl trimethoxy silane (commercially available from OSI under the trade designation A-174).

Appropriate titanates for use herein include titanium IV tetrakis[2,2-bis[(2-propenyloxy)methyl]-1-butanolato-0] [bis(ditridecylphosphito-0),dihydrogen]$_2$ (commercially available from Kenrich Petrochemical Inc., Bayonne, N.J. under the trade designation KR-55).

When used, the flowability agent may be used in an amount of 0 to about 5 weight percent, based on the total weight of the composition.

In addition, adhesion promoters, such as the silanes, glycidyl trimethoxysilane (commercially available from OSI under the trade designation A-187) or gamma-amino propyl triethoxysilane (commercially available from OSI under the trade designation A-1100), may be used.

Cyanate esters may also be used in the inventive compositions. The cyanate esters useful as a component in the inventive compositions may be chosen from dicyanatobenzenes, tricyanatobenzenes, dicyanatonaphthalenes, tricyanatonaphthalenes, dicyanatobiphenyl, bis(cyanatophenyl)methanes and alkyl derivatives thereof, bis(dihalocyanatophenyl)propanes, bis(cyanatophenyl)ethers, bis(cyanatophenyl)sulfides, bis(cyanatophenyl)propanes, tris(cyanatophenyl)phosphites, tris(cyanatophenyl)phosphates, bis(halocyanatophenyl)methanes, cyanated novolac, bis[cyanatophenyl (methylethylidene)]benzene, cyanated bisphenol-terminated thermoplastic oligomers, and combinations thereof.

More specifically, aryl compounds having at least one cyanate ester group on each molecule and may be generally m represented by the formula $Ar(OCN)_m$, where Ar is an aromatic radical and m is an integer from 2 to 5. The aromatic radical Ar should contain at least 6 carbon atoms, and may be derived, for example, from aromatic hydrocarbons, such as benzene, biphenyl, naphthalene, anthracene, pyrene or the like. The aromatic radical Ar may also be derived from a polynuclear aromatic hydrocarbon in which at least two aromatic rings are attached to each other through a bridging group. Also included are aromatic radicals derived from novolac-type phenolic resins—i.e., cyanate esters of these phenolic resins. Ar may also contain further ring-attached, non-reactive substituents.

Examples of such cyanate esters include, for instance, 1,3-dicyanatobenzene; 1,4-dicyanatobenzene; 1,3,5-tricyanatobenzene; 1,3-, 1,4-, 1,6-, 1,8-, 2,6- or 2,7- dicyanatonaphthalene; 1,3,6-tricyanatonaphthalene; 4,4'-dicyanato-biphenyl; bis(4-cyanatophenyl)methane and 3,3',5,5'-tetramethyl bis(4-cyanatophenyl)methane; 2,2-bis(3,5-dichloro-4-cyanatophenyl)propane; 2,2-bis(3,5-dibromo-4-dicyanatophenyl)propane; bis(4-cyanatophenyl)ether; bis(4-cyanatophenyl)sulfide; 2,2-bis(4-cyanatophenyl)propane; tris(4-cyanatophenyl)-phosphite; tris(4-cyanatophenyl) phosphate; bis(3-chloro-4-cyanatophenyl)methane; cyanated novolac; 1,3-bis[4-cyanatophenyl-1-(methylethylidene)]benzene and cyanated bisphenol-terminated polycarbonate or other thermoplastic oligomer.

Other cyanate esters include cyanates disclosed in U.S. Pat. Nos. 4,477,629 and 4,528,366, the disclosure of each of which is hereby expressly incorporated herein by reference; the cyanate esters disclosed in U.K. Pat. No. 1,305,702, and the cyanate esters disclosed in International Patent Publication WO 85/02184, the disclosure of each of which is hereby expressly incorporated herein by reference. Of course, combinations of these cyanate esters within the imidazole component of the compositions of the present invention are also desirably employed herein.

Particularly desirable cyanate esters for use herein are available commercially from Ciba Specialty Chemicals, Tarrytown, N.Y. under the tradename "AROCY" [1,1-di(4-cyanatophenylethane)]. The structures of three "AROCY" cyanate esters are shown below:

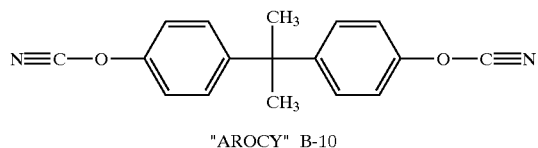

"AROCY" B-10

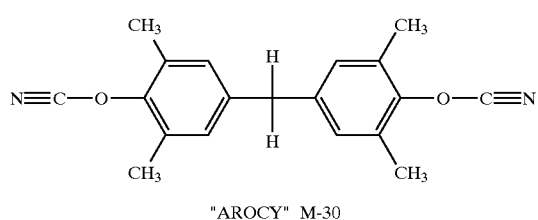

"AROCY" M-30

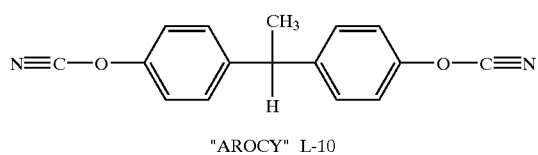

"AROCY" L-10

When used, the cyanate esters may be used in an amount of about 1 to about 20 weight percent, based on the total amount of the curable aromatic resin component.

Conventional additives may also be used in the compositions of the present invention to achieve certain desired physical properties of the composition, the cured reaction product, or both.

For instance, it may be desirable in certain instances (particularly where a large volume of inorganic filler component is used) to include a reactive co-monomer component for the epoxy resin component, such as a reactive diluent.

Appropriate reactive diluents for use herein may-include monofunctional or certain multifunctional epoxy resins. The reactive diluent should have a viscosity which is lower than that of the epoxy resin component. Ordinarily, the reactive diluent should have a viscosity less than about 250 cps. In the event such a monofunctional epoxy resin is included as a reactive diluent, such resin should be employed in an amount of up to about 50 weight percent, based on weight of the curable resin component.

The monofunctional epoxy resin should have an epoxy group with an alkyl group of about 6 to about 28 carbon atoms, examples of which include $C_{6-28}$ alkyl glycidyl ethers, $C_{6-28}$ fatty acid glycidyl esters and $C_{6-28}$ alkylphenol glycidyl ethers.

Commercially available monofunctional epoxy resin reactive diluents include those from Pacific Epoxy Polymers, Richmond, Mich., under the trade designations PEP-6770 (glycidyl ester of neodecandoic acid), PEP-6740 (phenyl glycidyl ether) and PEP-6741 (butyl glycidyl ether).

Commercially available multifunctional epoxy resin reactive diluents include these from Pacific Epoxy Polymers, under the trade designations PEP-6752 (trimethylolpropane triglycidyl ether) and PEP-6760 (diglycidyl aniline).

The compositions of the present invention may further contain other additives, such as defoaming agents, leveling agents, dyes, and pigments. Moreover, photopolymerization initiators may also be incorporated therein, provided that such initiators do not adversely affect the properties of the composition or reaction products formed therefrom.

The thermosetting resin compositions of the present invention may be of the one-pack type, in which all the ingredients are mixed together, or of the two-pack type in which the curable component(s), is(are) included in one part and the curing agent is stored separately in a second part, and mixed together only prior to use.

During a microelectronic underfill application, the thermosetting resin compositions according to the present invention penetrate and flow readily into the space between the semiconductor chip and the circuit board, or at least show a reduction in viscosity under heated or use conditions thus penetrating and flowing easily.

Reference to FIG. 1 shows a mounted structure (i.e., a FC package) in which a thermosetting resin composition of the present invention has been applied and cured.

The FC package 4 is formed by connecting a semiconductor chip (a bare chip) 2 to a carrier substrate 1 (e.g., a circuit board) and sealing the space therebetween suitably with a thermosetting resin composition 3.

More specifically, for example, in the assembly of FC semiconductor devices using SBB technology, the semiconductor chip 2 may be passed over a substrate bearing a conductive adhesive paste (such as a metal-filled epoxy) to form a layer thereof on the semiconductor chip 2. The layer is ordinarily formed by a printing mechanism. The conductive adhesive paste may be applied on either the carrier substrate or the semiconductor chip. One way to do this is with the stencil claimed and described in International Patent Publication No. PCT/FR95/00898. Alternatively, this connection may also be made by an anisotropically conductive adhesive. See International Patent Publication No. PCT/US97/13677.

Thereafter, the semiconductor chip 2 is positioned over the carrier substrate 1 in such a manner so that the semiconductor chip 2 is in alignment with the electrodes 5 and 6 on the carrier substrate 1, now coated with a patterned layer of conductive adhesive paste or solder, 7 and 8. The conductive adhesive paste may be cured by a variety of ways, though ordinarily a heat cure mechanism is employed.

In order to improve reliability, the space between the semiconductor chip 2 and the carrier substrate 1 is sealed with a thermosetting resin composition 3. The cured product of the thermosetting resin composition should completely fill that space.

The semiconductor chip ordinarily may be coated with a polyimide-, poly-benzocyclobutane- or silicone nitride-based material to passivate environmental corrosion.

Carrier substrates may be constructed from ceramic substrates of $Al_2O_3$, $SiN_3$ and mullite ($Al_2O_3$—$SiO_2$); substrates or tapes of heat-resistant resins, such as polyimides; glass-reinforced epoxy; ABS and phenolic substrates which are also used commonly as circuit boards; and the like. Any electrical connection of the semiconductor chip to the carrier substrate may be used, such as connection by a high-melting solder or electrically (or anisotropically) conductive adhesive and the like. In order to facilitate connections, particularly in SBB technology, the electrodes may be formed as wire bond bumps.

After the semiconductor chip is electrically connected to the carrier substrate, the resulting structure is ordinarily subjected to a continuity test or the like. After passing such test, the semiconductor chip may be fixed thereto with a thermosetting resin composition, as described below. In this way, in the event of a failure, the semiconductor chip may be removed before it is fixed to the carrier substrate with the thermosetting resin composition.

Using a suitable application means, such as a dispenser, a thermosetting resin composition in accordance with this invention is applied to the periphery of the electronically-connected semiconductor chip. The composition penetrates by capillary action into the space between the carrier substrate and the semiconductor chip.

The thermosetting resin composition is then thermally cured by the application of heat. During the early stage of this heating, the thermosetting resin composition shows a significant reduction in viscosity and hence an increase in fluidity, so that it more easily penetrates into the space between the carrier substrate and the semiconductor chip. Moreover, by preheating the carrier substrate, the thermosetting resin composition is allowed to penetrate fully into the entire space between the carrier substrate and the semiconductor chip.

Thermosetting resin compositions of the present invention may ordinarily be cured by heating to a temperature in the range of about 120 to about 180° C. for a period of time of about 0.5 to 30 minutes. However, generally after application of the composition, an initial cure time of about 1 minute sets up the composition, and complete cure is observed after about 5 to about 15 minutes at 165° C. Thus, the composition of the present invention can be used at relatively moderate temperatures and short-time curing conditions, and hence achieve very good productivity.

The amount of thermosetting resin composition applied should be suitably adjusted so as to fill almost completely the space between the carrier substrate and the semiconductor chip, which amount of course may vary depending on application.

Cured reaction products of the thermosetting resin compositions of the present invention demonstrate excellent adhesive force, heat resistance and electric properties, and acceptable mechanical properties, such as flex-cracking resistance, chemical resistance, moisture resistance and the like, for the applications for which they are used herein.

Figure 2:
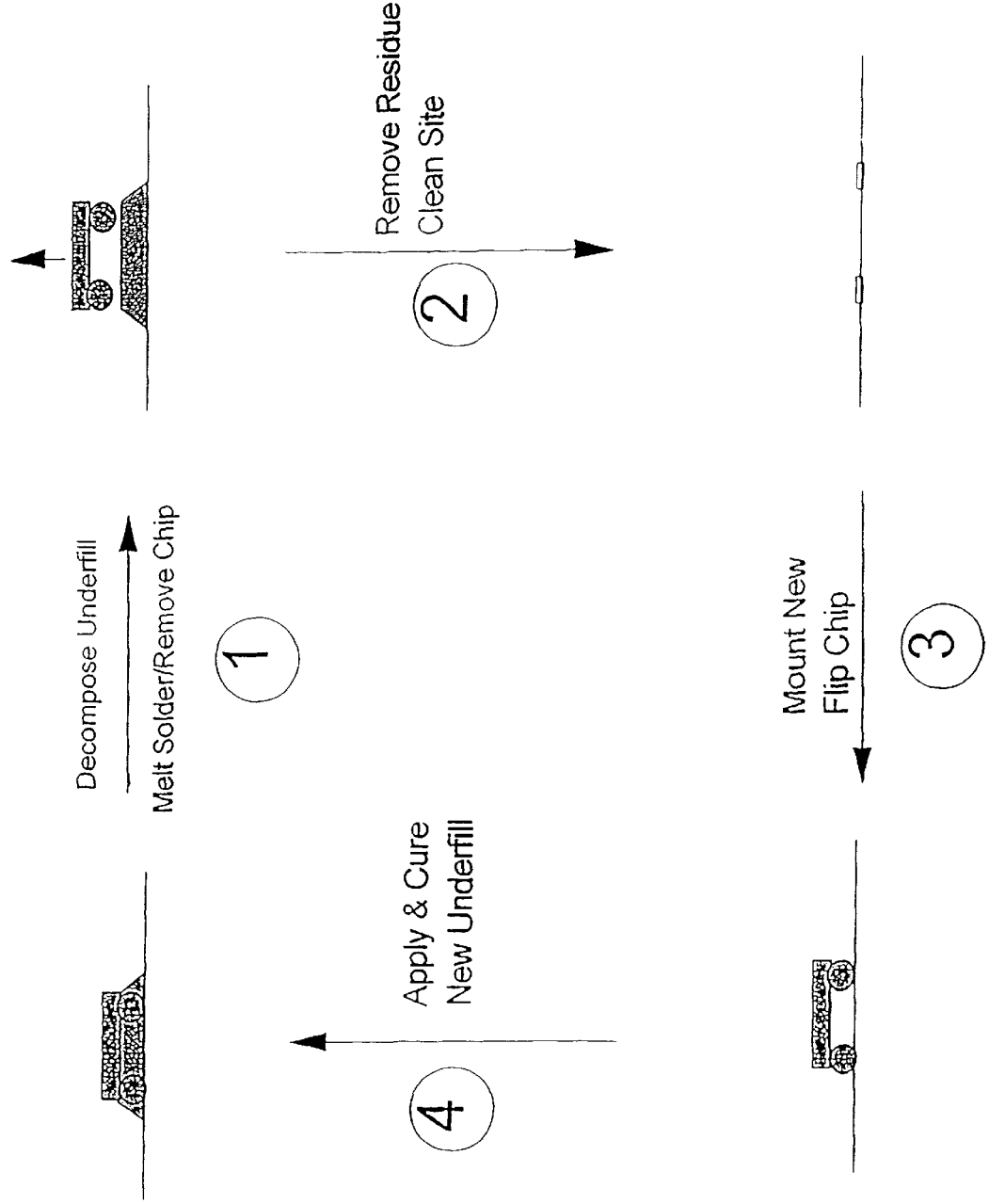
FIG. 2 depicts a flow diagram of a procedure useful to rework a cured thermosetting resin composition in accordance with the present invention, so as to remove a semiconductor device from a circuit board to which it had been attached.

In the mounting process by using the thermosetting resin composition of the present invention, after the semiconductor device is mounted on the circuit board as described above, the resulting structure is tested with respect to characteristics of the semiconductor device, connection between the semiconductor device and the circuit board, other electrical characteristics, and the state of sealing. In the event a failure is found, repair can be made in the following manner and as shown in the flow diagram depicted in FIG. 2.

The area around the semiconductor device which has failed is heated at a temperature of about 190 to about 260° C. for a period of time ranging from about 10 seconds to about 5 minutes. (See FIG. 2, step 1.) Desirably, the temperature should be maintained in the range of about 210 to about 220° C. and the period of time should be within the 30 seconds to 2 minute range. Although no particular limitation is placed on the way in which heating occurs, localized heating is particularly desirable, such as the application of hot air to the failure site by a heating gun.

As soon as the solder is melted and the resin is softened by partial decomposition to cause a reduction in bond strength, the semiconductor device may be pulled apart and removed from the substrate, such as with tweezers or pliers.

After the semiconductor device 4 is removed, a residue of the cured reaction product of the thermosetting resin composition and a residue of the solder are left on the circuit board 5. The residue of the cured product of the thermosetting resin composition can be removed, for example, by scraping it off after the residue has been softened by heating it to a predetermined temperature.

The residue of the solder can be removed, for example, by use of a solder-absorbing braided wire. (See FIG. 2, step 2.)

Finally, a new semiconductor chip may be mounted again onto the circuit board (which has been cleaned as described above) and re-fluxed. (See FIG. 2, step 3.) Following mounting, a thermosetting resin composition in accordance with this invention may be dispensed in the area between the semiconductor device and the circuit board. (See FIG. 2, step 4.) Repair of the failure site is thus completed.

Where a failure site is found in the circuit board, the semiconductor device can be reused by removing the residue of the cured reaction product of the thermosetting resin composition and the residue of the solder left on the bottom of the semiconductor device in the same manner as described above.

The present invention will be more readily appreciated with reference to the examples which follow.

EXAMPLES

In these examples, compositions in accordance with the present invention were prepared and evaluated for performance.

Figure 3:
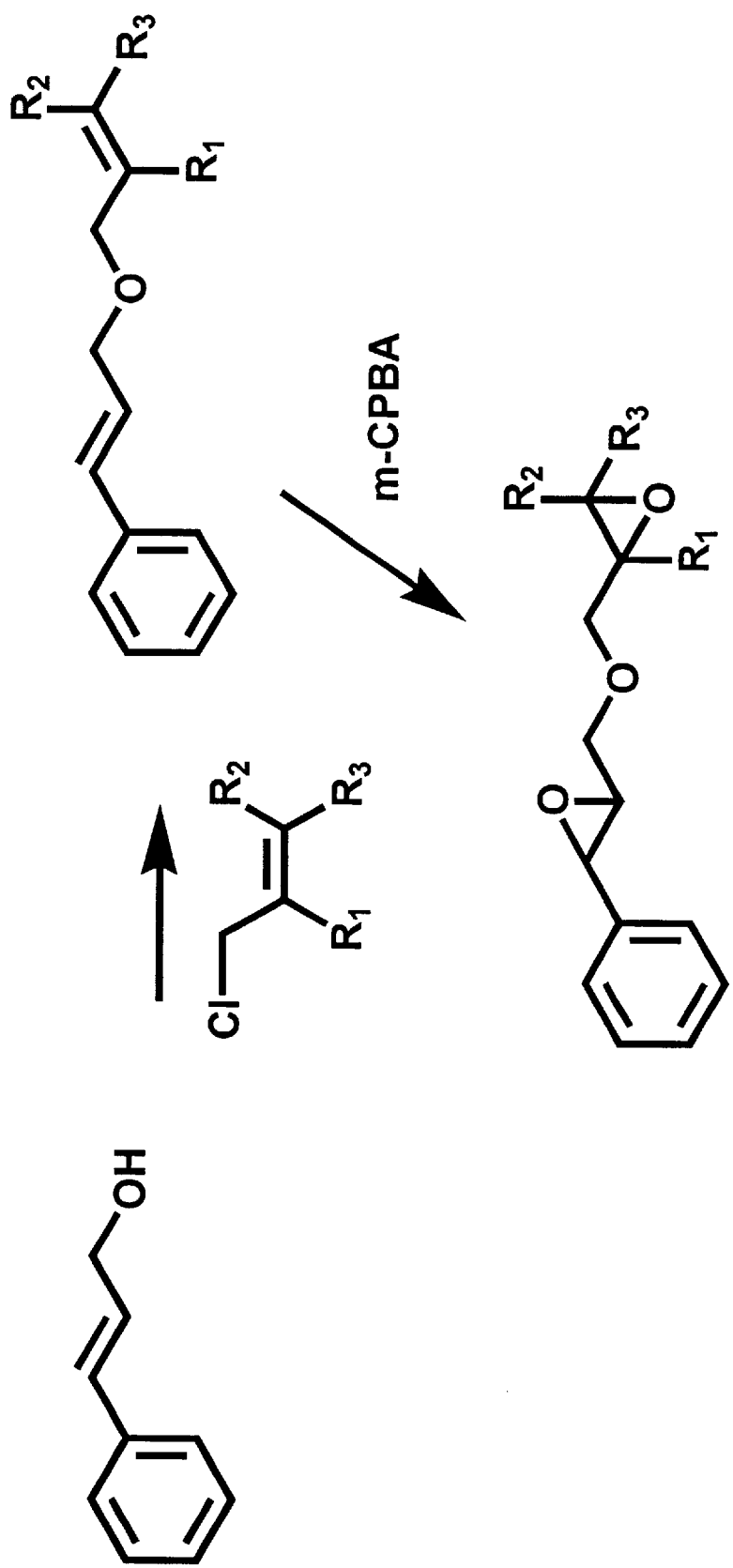
FIG. 3 depicts a general synthetic scheme for preparing the general epoxy- or episulfide-containing aromatic compound, represented by struture I and four specific compounds within that structure.
Figure 4:
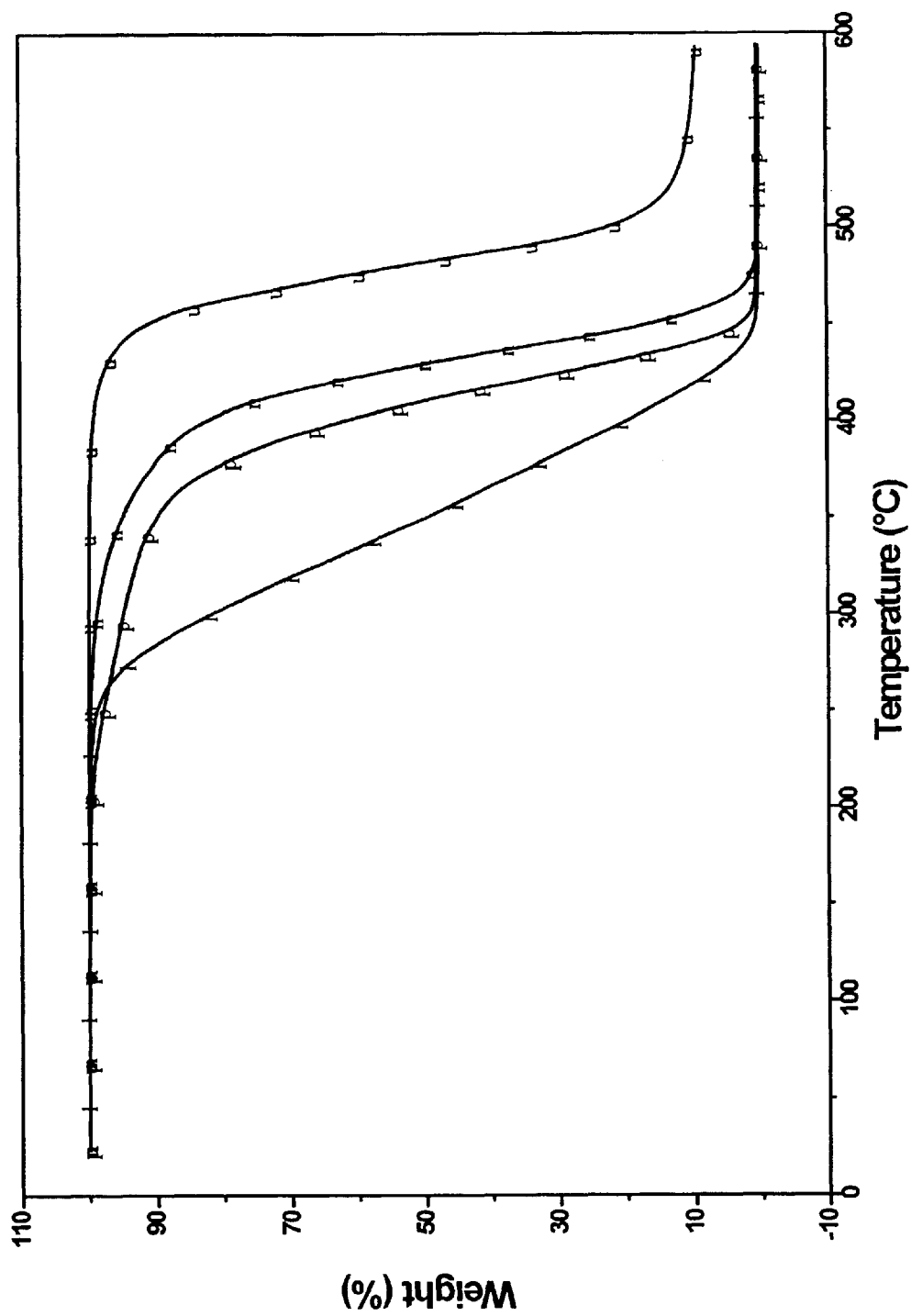
FIG. 4 depicts a TGA curve of cured reaction products of compositions based on COGE (square), Compound XVI of the '922 and '033 patents (closed circle), commercially available diepoxidized dicycloaliphatic ester (ERL 4221) (closed square) and commercially available diglycidyl ether of bisphenol F epoxy resin (RE-404-S)(closed diamond), cured with an anhydride curing agent.
Figure 5:
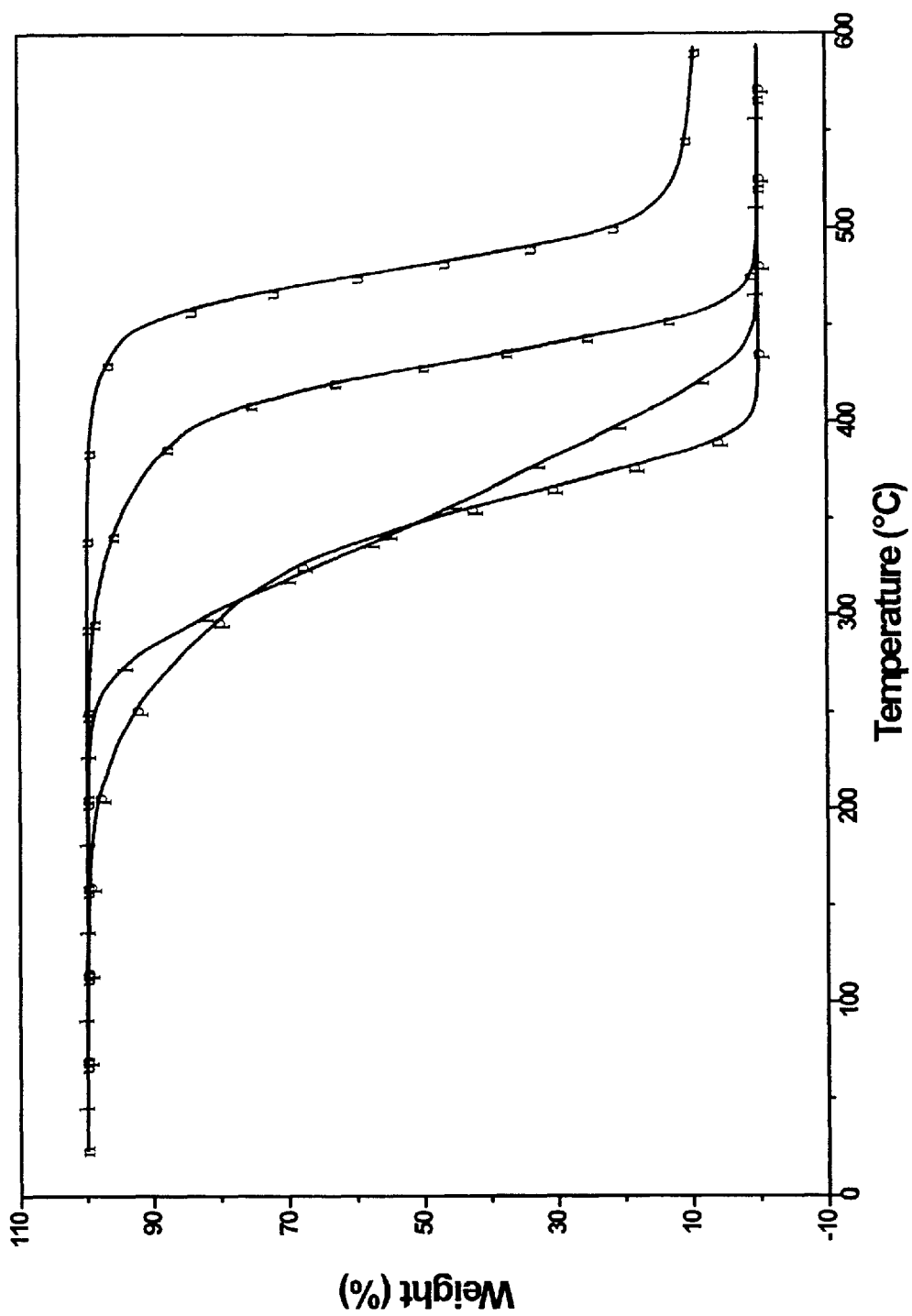
FIG. 5 depicts a TGA curve of cured reaction products of compositions based on COMPOE (square), Compound XVI of the '922 and '033 patents (closed circle), ERL 4221 (closed square) and RE-404-S (closed diamond), cured with an anhydride curing agent.
Figure 6:
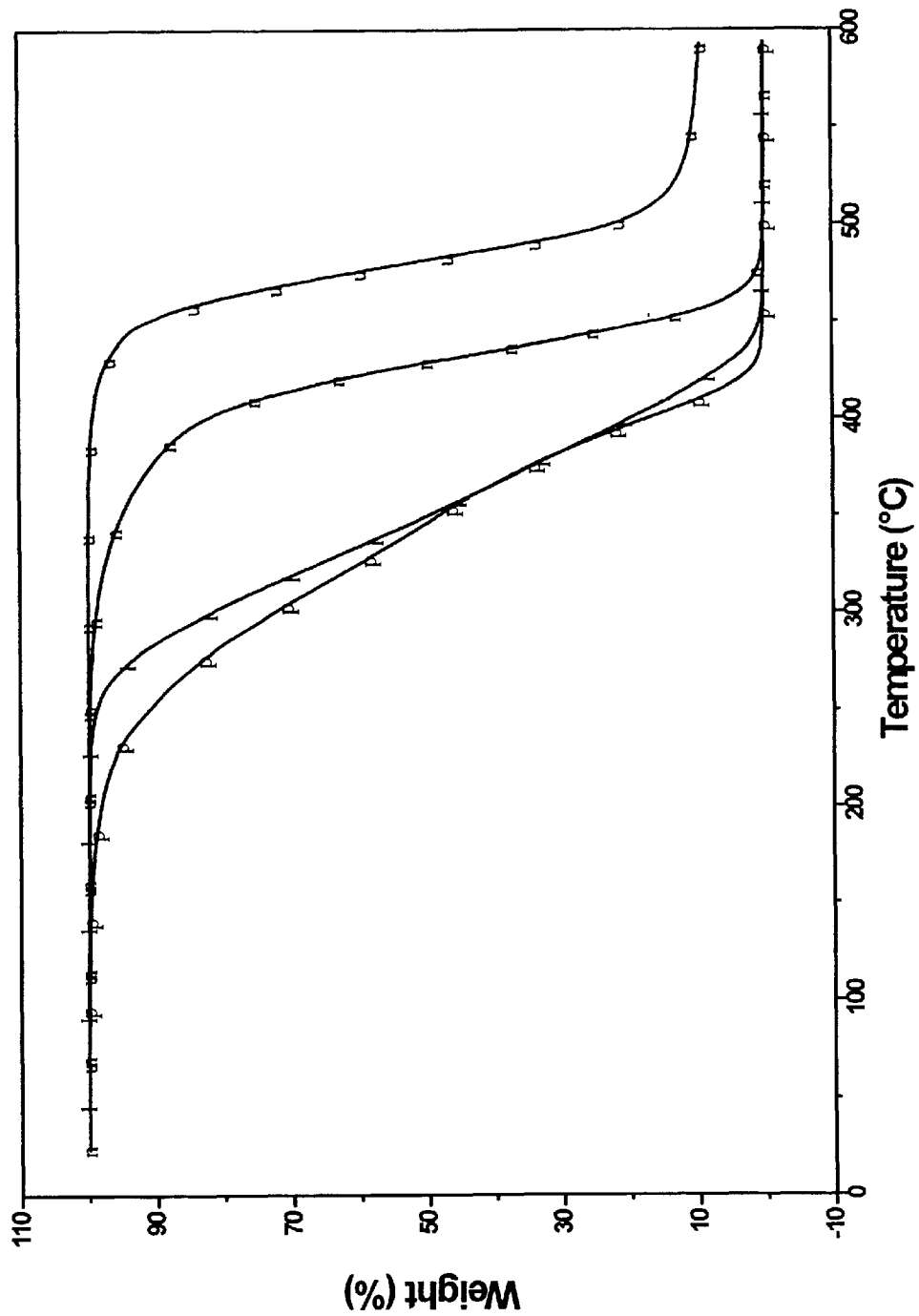
FIG. 6 depicts a TGA curve of cured reaction products of compositions based on COMBOE (square), Compound XVI of the '922 and '033 patents (closed circle), ERL 4221 (closed square) and RE-404-S (closed diamond), cured with an anhydride curing agent.
Figure 7:
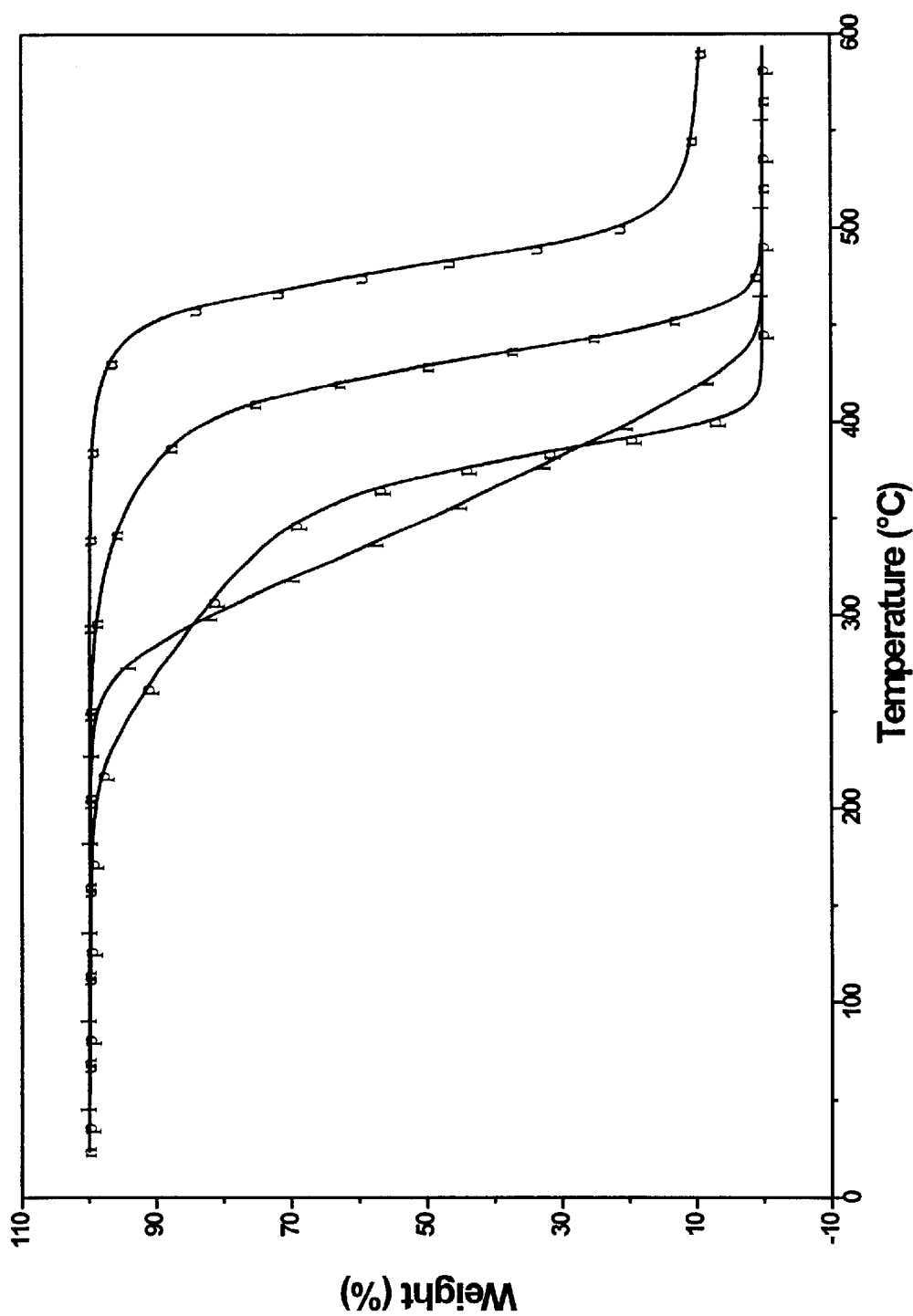
FIG. 7 depicts a TGA curve of cured reaction products of compositions based on di-COE (square), Compound XVI of the '922 and '033 patents (closed circle), ERL 4221 (closed square) and RE-404-S (closed diamond), cured with an anhydride curing agent.

Initally, however, COGE, COMPOE, COMBOE and di-COE were synthesized as described below (see also FIG. 3):

Synthesis
Cinnamyl Glycidyl Ether ("CGE")

To a four-neck 1000 ml round bottom flask, equipped with a mechanical stirrer, thermometer, and condenser, were added 50% w/w aqueous sodium hydroxide ("NaOH") (250 ml), epibromohydrin (56 g, 400 mmol), and tetrabutylammoniumhydrogen sulfate ("TBAHS") (5.2 g, 14.9 mmol). The mixture was stirred at room temperature for a period of time of about 20 minutes. To the mixture was added cinnamyl alcohol (50 g, 365 mmol), drop-wise over a period of time of about 60 minutes. The reaction was conducted at ice/water temperatures, and was allowed to continue overnight with stirring. Once the reaction was complete, the mixture was cooled and ice cold water (500 ml) was slowly added. The quenched reaction was allowed to stir for a period of time of about 30 minutes and then twice extracted with diethyl ether (250 ml). The organic portion was separated and twice washed with brine (250 ml), dried over anhydrous magnesium sulfate, filtered, and evaporated to dryness in vacuo. Crude CGE was obtained as a clear amber liquid (67.0 g), which was distilled in vacuo (119–135° C. at 820 mTorr) to provide CGE (48.1 g, 247.8 mmol), as a clear colorless liquid. G.C. 98.0% (retention time 8.10 min.). $^1$H NMR (CDCl$_3$) δ7.2–7.4 (br m, 5, C$_6$H$_5$), 6.65 (d, 1, —CH═), 6.25 (m, 1, ═CH—), 4.2 (br m, 2, CH$_2$), 3.75 and 3.20 (d, 2, CH$_2$), 3.45 (m, 1, OCH), 2.8 and 2.6 (d, 2, OCH$_2$). FT-IR (neat) 3081, 3057, 3025, 2999, 2922, 2855, 1495, 1448, 1253, 1115, 969, 902, 855, 746, 694.

Cinnamyl Oxide Glycidyl Ether ("COGE")

To a four neck 500 ml round bottom flask equipped with a mechanical stirrer, thermometer and condenser, were added CGE (48.1 g, 247.8 mmol), and dichloromethane (250 ml). To the solution was added 70% (m-chloroperoxybenzoic acid (63.9 g, 259.4 mmol) in small portions over a period of time of about two hours, at a reaction temperature maintained below at about 10° C. with an ice water bath. As the reaction proceeded, m-chlorobenzoic acid precipitated from solution. The mixture was stirred overnight and kept below 20° C. in an ice water bath. The reaction completion was confirmed. The precipitated solid was filtered and the organic layer was washed consecutively twice each with 10% aqueous sodium sulfate (200 ml), sodium bicarbonate (200 ml) and water (200 ml). The organic portion was separated, dried over anhydrous magnesium sulfate, filtered and concentrated in vacuo to constant weight to provide crude COGE (48.9 g), as a pale liquid. Crude COGE was then distilled in vacuo (128–133° C. at 745 mTorr) to provide distilled COGE (45.1 g, mmol), as a clear colorless liquid. G.C. 97.5% (retention time 8.72 min.). $^1$H NMR (CDCl$_3$) δ7.2–7.4 (br m, 5, C$_6$H$_5$), 3.80–3.95 (m, 3, CH$_2$ and CH), 3.7 and 3.5 (m, 2, CH$_2$), 3.2 (m, 2, OCH), 2.8 and 2.65 (d, 2, OCH$_2$). FT-IR (neat) 3057, 2996, 2891, 1605, 1463, 1339, 1253, 1107, 881, 767, 699, 615.

Cinnamyl Methyl Propene Ether ("CMPE")

To a four-neck 1000 ml round bottom flask, equipped with a mechanical stirrer, thermometer, and condenser, was added 50% w/w aqueous NaOH (250 ml), 1-chloro-2-methyl-2-propene (37 g, 400 mmol), and TBAHS (5.2 g, 14.9 mmol). The mixture was stirred at room temperature for a period of time of about 20 minutes. To the mixture was added cinnamyl alcohol (50 g, 365 mmol), drop-wise over a period of time of about 60 minutes. The reaction was conducted at ice/water bath temperatures, and allowed to continue with stirring overnight. Once the reaction was complete, the mixture was cooled and ice cold water (500 ml) was slowly added. The quenched reaction was allowed to stir for a period of time of about 30 minutes and then twice extracted with dichloromethane (250 ml). The organic portion was separated and twice washed with brine (250 ml), dried over anhydrous magnesium sulfate, filtered, and evaporated to dryness in vacuo. Crude CMPE was obtained as an amber liquid (75.2 g), which was distilled in vacuo (86–94° C. at 730–740 mTorr) to provide distilled CMPE (59.8 g, mmol), as a clear slightly colored liquid. G.C. 92.1% (retention time 7.19 min.). $^1$H NMR (CDCl$_3$) δ7.2–7.4 (br m, 5, C$_6$H$_5$), 6.6 (d, 1, CH═), 6.3 (m, 1, CH═), 4.9 and 5.0 (s, 2, ═CH$_2$), 4.15 (d, 2, CH$_2$), 3.95 (s, 2, CH$_2$), 1.75 (s, 3, —CH$_3$). FT-IR (neat) 3081, 3060, 3027, 2974, 2915, 2849, 1658, 1496, 1448, 1363, 1116, 1078, 966, 900, 743, 692.

Cinnamyl Oxide Methyl Propene Oxide Ether ("COMPOE")

To a four neck 500 ml round bottom flask equipped with a mechanical stirrer, thermometer and condenser, were added cinnamyl methyl propene ether (59.8 g, 311.8 mmol), and dichloromethane (250 ml). To the solution was added 70% m-chloroperoxybenzoic acid (162.5 g, 659.2 mmol) portionwise over a period of time of about two hours. The reaction temperature was maintained below about 10° C. with an ice water bath. As the reaction proceeded, m-chlorobenzoic acid precipitated from solution. The mixture was stirred overnight and maintained at a temperature below about 20° C. in an ice water bath. The precipitated solid was filtered and the organic portion was washed consecutively twice each with 10% aqueous sodium sulfate (200 ml), sodium bicarbonate (200 ml) and water (200 ml). The organic portion was separated, dried over anhydrous magnesium sulfate and filtered. The organic portion was concentrated in vacuo to constant weight to provide crude COMPOE (64.8 g), as a pale white liquid. It was then distilled in vacuo (138–152° C. at 777 mTorr) to provide distilled COMPOE (40.2 g, mmol), as a clear slightly yellow liquid. G.C. 95.9% (retention time 8.72 min.). $^1$H NMR (CDCl$_3$) δ7.2–7.4 (br m, 5, C$_6$H$_5$), 3.4–3.9 (m, 4, CH$_2$), 3.75 (d, 1, CH), 3.2 (m, 1, CH), 2.6 and 2.8 (s, 2, OCH$_2$), 1.4 (s, 3, CH$_3$) FT-IR (neat) 3033, 2986, 2926, 2865, 1462, 1114, 883, 811, 752, 699.

Cinnamyl Methyl Butene Ether ("CMBE")

To a four-neck 1000 ml round bottom flask, equipped with a mechanical stirrer, thermometer, and condenser, were added 50% w/w aqueous NaOH (250 ml), 1-chloro-3-methyl-2-butene (44 g, 400 mmol), and TBAHS (5.2 g, 14.9 mmol). The mixture was stirred at room temperature for a period of time of about 20 minutes. To the mixture was added cinnamyl alcohol (50 g, 365 mmol), drop-wise over a period of time of about 60 minutes. The reaction temperature was maintained below about 30° C. with an ice water bath, and was allowed to stir overnight. Once the reaction was complete, the mixture was cooled and ice cold water (500 ml) was slowly added. The quenched reaction was allowed to stir for a period of time of about 30 minutes and then twice extracted with diethyl ether (250 ml). The organic portion was separated and twice washed with brine (250 ml), dried over anhydrous magnesium sulfate, filtered, and evaporated to dryness in vacuo. Crude CMBE (75.1 g) was obtained as a clear amber liquid which was distilled in vacuo (90–108° C. at 770 mTorr) to provide distilled CMBE (58.5 g, mmol), 82.5% of theoretical yield), a clear slightly colored liquid. G.C. 78.9% (retention time 8.30 min.). $^1$H NMR (CDCl$_3$) δ7.2–7.4 (br m, 5, C$_6$H$_5$), 6.6 (d, 1, CH), 6.3 (m, 1, CH), 5.4 (m, 1, CH), 4.1 (d, 2, CH$_2$), 4.0 (d, 2, CH$_2$), 1.70 & 1.75 (s, 6, CH$_3$) FT-IR (neat) 3082, 3060, 3026, 2972, 2913, 2854, 1661, 1495, 1448, 1377, 1115, 1075, 966, 742, 692.

Cinnamyl Oxide Methyl Butene Oxide Ether ("COMBOE")

To a four neck 500 ml round bottom flask equipped with mechanical stirrer, thermometer and condenser, were added cinnamyl methyl butene ether (58.5 g, 260.2 mmol), and dichloromethane (250 ml). To the solution was added 70% m-chloroperoxybenzoic acid (132.8 g, 538.7 mmol) portionwise over a period of time of about two hours. The reaction temperature was maintained below about 10° C. with an ice water bath. As the reaction proceeded, m-chlorobenzoic acid precipitated from solution. The mixture was stirred overnight and maintained at a temperature below aboout 20° C. in an ice water bath. The precipitated solid was filtered and the organic portion was washed consecutively twice each with 10% aqueous sodium sulfate (200 ml), sodium bicarbonate (200 ml) and water (200 ml). The organic portion was separated, dried over magnesium sulfate and filtered. The organic portion was concentrated in vacuo to constant weight to provide crude COMBOE (61.4 g), as a pale white liquid. Crude COMBOE was then distilled in vacuo (132–148° C. at 776 mTorr) to provide distilled COMBOE (44.3 g, mmol) as a clear colorless liquid. G.C. 58.60% (retention time 9.16 min.). $^1$H NMR (CDCl$_3$) δ7.2–7.4 (br m, 5, C$_6$H$_5$), 3.55–3.9 (m, 4, CH$_2$), 3.75 (d, 1, OCH), 3.2 (m, 1, OCH), 3.0 (m, 1, OCH), 1.3 (d, 6, CH$_3$). FT-IR (neat) 3063, 3029, 2964, 2866, 1725, 1457, 1380, 1247, 1108, 881, 752, 699, 615.

Di-Cinnamyl Ether ("di-CE")

To a four-neck 1000 ml round bottom flask, equipped with a mechanical stirrer, thermometer, and condenser, were added 50% w/w aqueous NaOH (250 ml), cinnamyl bromide (80.44 g, 400 mmol), and TBAHS (5.2 g, 14.9 mmol). The mixture was stirred at room temperature for a period of time of about 20 minutes. To the mixture was added cinnamyl alcohol (50 g, 365 mmol), drop-wise over a period of time of about 60 minutes. The reaction was maintained at a temperature below about 30° C. with an ice water bath, and allowed to stir overnight. Once the reaction was complete, the mixture was cooled and ice cold water (500 ml) was slowly added. The quenched reaction was allowed to stir for a period of time of about 30 minutes and then twice extracted with dichloromethane (250 ml). The organic portion was separated and twice washed with brine (250 ml), dried over anhydrous magnesium sulfate, filtered, and evaporated to dryness in vacuo. Crude di-CE (96.0 g) was obtained as an amber liquid that was distilled in vacuo (175–180° C. at 775 mTorr) to provide distilled di-CE (75.0 g, mmol) as a clear yellow liquid. G.C. 87.1% (retention time 11.95 min.). $^1$H NMR (CDCl$_3$) δ7.2–7.4 (br m, 10, C$_6$H$_5$), 6.65 (d, 2, CH), 6.35 (m, 2, CH), 4.2 (d, 4, CH$_2$). FT-IR (neat) 3081, 3058, 3026, 2928, 2845, 1677, 1495, 1448, 1360, 1124, 1072, 969, 742, 693.

Di-Cinnamyl Oxide Ether ("di-COE")

To a four neck 500 ml round bottom flask equipped with a mechanical stirrer, thermometer and condenser, were added di-cinnamyl ether (75.0 g, 260.6 mmol), and dichloromethane (250 ml). To the solution was added 70% m-chloroperoxybenzoic acid (135.8 g, 550.9 mmol) portion-wise over a period of about 2 hours. The reaction temperature was maintained at a temperature below about 10° C. with an ice water bath. As the reaction proceeded, m-chlorobenzoic acid precipitated from solution. The mixture was stirred overnight at a temperature maintained below about 20° C. in an ice water bath. The precipitated solid was filtered and the organic portion was washed consecutively twice each with 10% aqueous sodium sulfate (200 ml), sodium bicarbonate (200 ml) and water (200 ml). The organic portion was separated, dried over anhydrous magnesium sulfate and filtered. The organic portion was concentrated in vacuo to constant weight to provide crude di-COE as a yellow oil, (73.3 g), which solidified upon standing. The solid was dissolved in hot ethanol (250 ml), gravity filtered and allowed to re-crystallize overnight at room temperature, providing a white crystalline solid, di-COE (40.6 g). A second crop was gathered from the filtrate to provide an off-white crystalline solid (12.8 g) of similar quality. G.C.>76.2% (retention time 12.89 min.). $^1$H NMR (CDCl$_3$) δ7.2–7.4 (br m, 10, C$_6$H$_5$), 3.95 and 3.75 (m, 4, CH$_2$), 3.8 (s, 2, OCH), 3.25 (m, 2, OCH). FT-IR (neat) 3087, 3060, 3031, 2987, 2923, 2891, 2858, 1459, 1115, 870, 767, 697, 619.

Thermosetting Resin Composition

Thermosetting resin compositions in accordance with this invention were prepared by mixing together for a period of time of about 10 minutes at room temperature in an open vessel the following components in the order noted in Table 1.

TABLE 1

| COMPONENTS | | Sample No./Amt. (phr) | | | | | | |
|---|---|---|---|---|---|---|---|---|
| TYPE | IDENTITY | 1 | 2 | 3 | 4 | 5 | 6 | 7 |
| Epoxy | RE-404-S | 100 | — | — | — | — | — | — |
| | ERL-4221 | — | 100 | — | — | — | — | — |
| | Compound XVI* | — | — | 100 | — | — | — | — |
| | COGE | — | — | — | 100 | — | — | — |
| | COMPOE | — | — | — | — | 100 | — | — |
| | COMBOE | — | — | — | — | — | 100 | — |
| | di-COE | — | — | — | — | — | — | 100 |
| Curing | MHHPA | 90 | 90 | 90 | 90 | 90 | 90 | 90 |
| Agent | Ethylene Glycol | 2 | 2 | 2 | 2 | 2 | 2 | 2 |
| | PhCH$_2$NMe$_2$ | 1.5 | 1.5 | 1.5 | 1.5 | 1.5 | 1.5 | 1.5 |

*Compound XVI — U.S. Pat. Nos. 5,948,922 (Ober) and 5,973,033 (Ober)

Sample Nos. 1–3 were used as controls, with the commercially available bisphenol-F-type epoxy resin (from Nippon Kayaku under the trade designation RE-404-S) used as the curable resin in Sample No. 1, the commercially available 3,4-epoxycyclohexylmethyl-3,4-epoxycyclohexane-carboxylate (from Union Carbide under the trade designation, ERL-4221), as the curable resin for Sample No. 2, and Compound XVI disclosed in U.S. Pat. No. 5,948,922 (Ober) and U.S. Pat. No. 5,973,033 (Ober), as the curable resin for Sample No. 3.

Sample Nos. 4–7 were prepared with epoxy-containing aromatic compounds in accordance with this invention.

Cure Conditions

Sample Nos. 1–7 were cured by exposure to temperature conditions of 100° C. for a period of time of 2 hours, followed by exposure to temperture conditons of 140° C. for a period of time of 6 hours.

Physical Properties

The compositions have a variety of properties in both the uncured and cured state which are measurable and useful parameters for the end user in choosing a particular formulation for a desired need.

For instance, in reaching the cured state, the cure schedule is of interest. The cure schedule refers to the time required for the onset of cure to occur at a certain temperatrue, in a specified period of time. This may be measured by differential scanning calorimetry ("DSC").

In the cured state, a variety of properties are useful depending on the end use for which the composition is destined. For instance, adhesion provides information on the strength of the bond formed by the cured reaction product. In an adhesion evaluation, die shear adhesion may be measured by a Sebastian 5 die shear measurement instrument, which measures the amount of shear strength (in psi) required to pull apart a die attached to a circuit board with about two milligrams of the cured reaction product as an underfill sealant (without a solder mask, or chipbonding adhesive).

Reworkability determines the ease with which a cured reaction product may be controllably degraded. The extent to which the cured reaction product loses mass over time at an increase in temperature may be measured by thermal gravimetric analysis ("TGA"), and provides information on the temperature (or range) at which the cured reaction product degrades.

Reference to FIGS. 4–7 show TGA data for cured reaction products of Sample Nos. 1–7 using an anhydride curing agent, compared with TGA data for cured reaction products of compositions based on the commercially available epoxies RE-404-S (Sample No. 1) and ERL-4221 (Sample No. 2), and Compound XVI of the '922 and '033 patents (Sample No. 3).

The TGA data indicate that cured reaction products of the inventive compositions (Sample Nos. 4–7) degrade and lose mass at a temperature lower than cured reaction products of the compositions based on either of the commercially available epoxies (Sample Nos. 1 and 2).

REWORKABILITY

Perhaps most significant is the temperature range at which the epoxy-based compositions of the present invention degrade. That is, with the recent interest in preparing underfill encapulants that cure at temperatures below those used during the solder reflow process and degrade at temperatures in excess of those of the solder relow process, the compositions of the present invention achieve this objective without reaching temperatures that may compromise the integrity of the semiconductor devices attached to the current branch.

Practical reworkability may be demonstrated using a hot air generator to heat the area around the die, fixed to the circuit board with the compositions of any of Sample Nos. 4–7, to an air temperature of about 280° C., with a die temperature of about 215–220° C. for a period of time of about 2 minutes. Then, the die may be easily removed by pulling or twisting the die from the circuit board using tweezers in a period of time of about 30 seconds. The circuit board may then be cleaned using a dremel at about 25,000–30,000 rpm, followed by application of a flat-end horse hair brush. The circuit board cleaning ordinarily occurs within a period of time of about 2 minutes.

The site of the failed semiconductor chip should then be fluxed and a new semiconductor chip may be attached using conventional flip chip technology. Then, the thermosetting resin composition of this invention may be applied around the periphary of the newly-replaced semi-conductor chip and cured by heating to an appropriate temperature, as described herein.

The samples described above are presented as illustrative, rather than limiting, examples of the inventive compositions. Many additional embodiments thereof are included in the spirit and scope of the invention, which are defined by the claims.

What is claimed is:

1. A thermosetting resin composition, reaction products of which are capable of softening and losing their adhesiveness under exposure to temperature conditions in excess of those used to cure the composition, said composition comprising:

(a) a curable resin component, at least a portion of which comprises an epoxy- or episulfide-containing aromatic compound within the following formula:

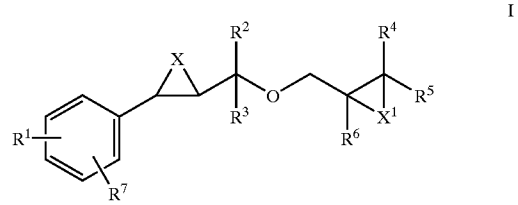

wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methyl, ethyl, propyl, butyls, phenyl, benzyl, phenoxy, benzyloxy, and when $R^5$ and $R^6$ are present, and taken together, may form a cyclic, bicyclic or heterocyclic structure, which may be substituted by straight chain or branched alkyl groups of from 1 to about 6 carbon atoms, or straight chain or branched alkenyl groups of from 2 to about 6 carbon atoms, and X and $X^1$ each are independently selected from oxygen and sulfur; and (b) a curing agent component.

2. The composition according to claim 1, wherein the epoxy-containing aromatic compound is within the following formula:

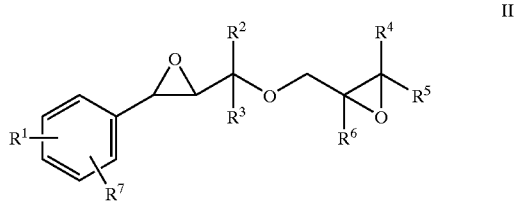

wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methyl, ethyl, propyls, butyls, phenyl, benzyl, phenoxy, benzyloxy and when $R^5$ and $R^6$ are present taken together, may form a cyclic, bicylic or heterocyclic structure, which may be substituted by straight chain or branched alkyl groups of from 1 to about 6 carbon atoms, or straight chain or branched alkenyl groups of 2 to about 6 carbon atoms; and (b) a curing agent component.

3. The composition according to claim 1, wherein the epoxy-containing aromatic compound is a member selected from the group consisting of:

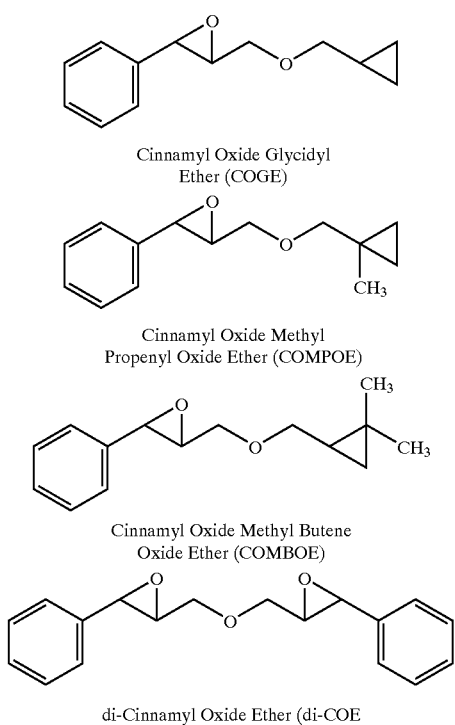

Cinnamyl Oxide Glycidyl Ether (COGE)

Cinnamyl Oxide Methyl Propenyl Oxide Ether (COMPOE)

Cinnamyl Oxide Methyl Butene Oxide Ether (COMBOE)

di-Cinnamyl Oxide Ether (di-COE

4. The composition according to claim 1, wherein the episulfide-containing aromatic compound is within the following formula:

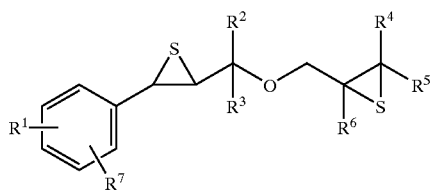

III wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methy, ethyl, propyls, butyls, phenyl, benzyl, phenoxy, benzyloxy and when $R^5$ and $R^6$ are present taken together, may form a cyclic, bicyclic or heterocyclic structure, which may be substituted by straight chain or branched alkyl groups of from 1 to about 6 carbon atoms, or straight chain branched alkenyl groups of 2 to about 6 carbon atoms; and (b) a curing agent component.

5. The composition according to claim 1, wherein the episulfide-containing aromatic compound is a member selected from the group consisting of:

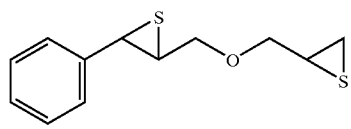

Cinnamyl Episulfide Thioglycidyl Ether

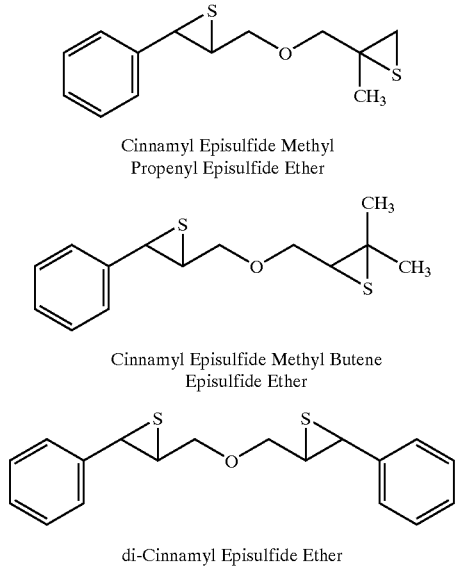

Cinnamyl Episulfide Methyl Propenyl Episulfide Ether

Cinnamyl Episulfide Methyl Butene Episulfide Ether di-Cinnamyl Episulfide Ether

6. The composition according to claim 1, wherein the epoxy- or episulfide-containing aromatic compound is selected from the group consisting of members within the following formula:

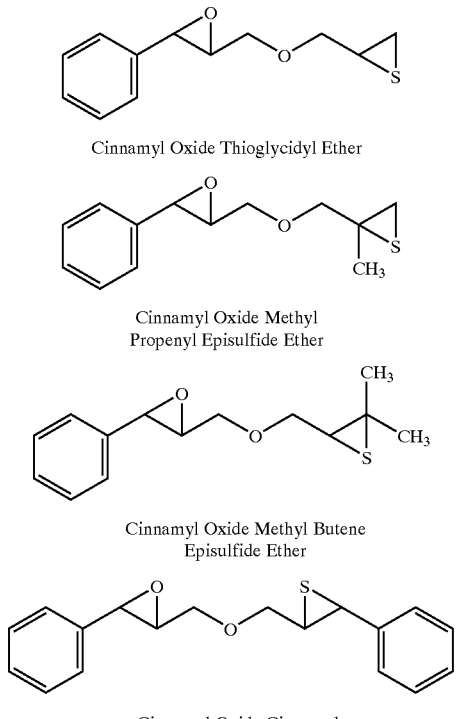

Cinnamyl Oxide Thioglycidyl Ether

Cinnamyl Oxide Methyl Propenyl Episulfide Ether

Cinnamyl Oxide Methyl Butene Episulfide Ether

Cinnamyl Oxide Cinnamyl Episulfide Ether

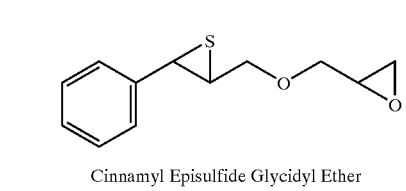

Cinnamyl Episulfide Glycidyl Ether

-continued

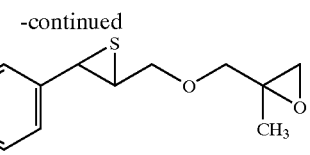

Cinnamyl Episulfide Methyl
Propenyl Oxide Ether

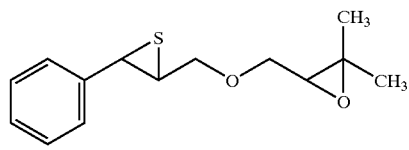

Cinnamyl Episulfide Methyl Butene
Oxide Ether

7. The composition according to claim 1, wherein the curing agent component is a member selected from the group consisting of anhydride compounds, aza compounds, amine compounds, amide compounds, imidazole compounds, and combinations thereof.

8. The composition according to claim 1, further comprising an inorganic filler component.

9. The composition according to claim 8, wherein the inorganic filler component is a member selected from the group consisting of materials constructed of or containing reinforcing silicas, aluminum oxide, silicon nitride, aluminum nitride, silica-coated aluminum nitride, boron nitride, and combinations thereof.

10. The composition according to claim 1, further comprising a flowability agent.

11. The composition according to claim 10, wherein the flowability agent is a member selected from the group consisting of silanes, titanates and combinations thereof.

12. The composition according to claim 10, wherein the flowability agent is selected from octyl trimethoxy silane, methacryloxy propyl trimethoxy silane, titanium IV tetrakis [2,2-bis[(2-propenyloxy)methyl]-1-butanolato-0][bis(ditridecylphosphito-0), dihydrogen]$_2$, and combinations thereof.

13. The composition according to claim 1, further comprising an adhesion promtor.

14. The composition according to claim 13, wherein the adhesion promoter is a member selected from the group consisting of glycidyl trimethoxysilane, gamma-amino propyl triethoxysilane, and combinations thereof.

15. The composition according to claim 1, further comprising a cyanate ester.

16. The composition according to claim 15, wherein the cyanate ester is a member selected from the group consisting of dicyanatobenzenes, tricyanatobenzenes, dicyanatonaphthalenes, tricyanatonaphthalenes, dicyanatobiphenyl, bis(cyanatophenyl)methanes and alkyl derivatives thereof, bis(dihalocyanatophenyl)propanes, bis(cyanatophenyl)ethers, bis(cyanatophenyl)sulfides, bis(cyanatophenyl)propanes, tris(cyanatophenyl)phosphites, tris(cyanatophenyl)phosphates, bis(halocyanatophenyl)methanes, cyanated novolac, bis[cyanatophenyl(methylethylidene)]benzene, cyanated bisphenol-terminated thermoplastic oligomers, and combinations thereof.

17. The composition according to claim 7, wherein the anhydride compounds may be selected from the group consisting of hexahydrophthalic anhydride, methyl hexahydrophthalic anhydride, 5-(2,5-dioxotetrahydrol)-3-methyl-3-cyclohexene-1,2-dicarboxylic anhydride, and combinations thereof.

18. The composition according to claim 7, wherein the aza compounds may be selected from the group consisting of

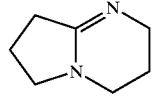

1, 5-Diazabicyclo [4.3.0] non-5-ene

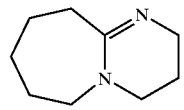

1, 8-Diazabicylco [5.4.0] undec-5-ene (DBU

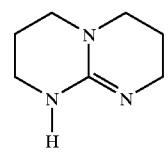

1, 5, 7-Triazabicyclo [4.4.0] dec-5-ene

Quinuclidine

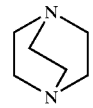

1, 4-Diazabicyclo [2.2.2] octane

19. The composition according to claim 7, wherein the amine compounds may be selected from the group consisting of dicyandiamide, diethylenetriamine, triethylenetetramine, diethylaminopropylamine, m-xylenediamine, diaminodiphenylamine, isophoronediamine, menthenediamine, polyamides, and combinations thereof.

20. The composition according to claim 1, wherein the amide compounds may be dicyandiamide.

21. The composition according to claim 1, wherein the imidazole compounds may be selected from the group consisting of imidazole, isoimidazole, 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-1-cyanoethyl-2-undecylimidazole, 1-cyanoethyl-2-phenylimidazole, 1-guanaminoethyl-2-methylimidazole, addition products of an imidazole and trimellitic acid, addition products of an imidazole and 2-n-heptadecyl-4-methylimidazole, phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4, 2-naphthyl-4,5-diphenylimidazole, 1-benzyl-2-methylimidazole, 2-p-methoxystyrylimidazole, and combinations thereof.

22. The composition according to claim 8, wherein the curable resin component is present in an amount within the range of about 10 to about 70 weight percent, based on the total weight of the composition, of which about 10 to about 75 weight percent thereof is comprised of an epoxy- or episulfide-containing aromatic compound according to claim 1; the curing agent component is present in an amount within the range of 3 to about 100 weight percent, based on the total weight of the epoxy resin component; the inorganic filler component is present in an amount up to about 70 weight percent, based on the total weight of the composition; and further comprising (d) a flowability agent, present in an amount up to about 0.5 weight percent, based on the total weight of the composition.

23. The composition according to claim 1, capable of sealing underfilling between a semiconductor device including a semiconductor chip mounted on a carrier substrate and a circuit board to which said semiconductor device is electrically connected or a semiconductor chip and a circuit board to which said semiconductor chip is electrically connected.

24. Reaction products formed from the compositions according to claim 1.

25. An electronic device comprising a semiconductor device and a circuit board to which said semiconductor device is electrically connected or a semiconductor chip and a circuit board to which said semiconductor chip is electrically connected, assembled using a thermosetting resin composition according to claim 1 as an underfill sealant between the semiconductor device and the circuit board or the semiconductor chip and the circuit board, respectively, wherein reaction products of the composition are capable of softening and losing their adhesiveness under exposure to temperature conditions in excess of those used to cure the composition.

26. A method of sealing underfilling between a semiconductor device including a semiconductor chip mounted on a carrier substrate and a circuit board to which said semiconductor device is electrically connected or a semiconductor chip and a circuit board to which said semiconductor chip is electrically connected, the steps of which comprise:
   (a) dispensing into the underfilling between the semiconductor device and the circuit board or the semiconductor chip and the circuit board a composition in accordance with claim 1; and
   (b) exposing the composition as so dispensed to conditions appropriate to cause the composition to form a reaction product.

27. A method of reworking a reaction product of a composition in accordance with claim 1, a step of which comprises:
   (a) exposing the reaction product to conditions appropriate to cause the reaction product to soften and lose adhesiveness.

28. The method according to claim 27, wherein the reaction product seals the underfilling between a semiconductor device including a semiconductor chip mounted on a carrier substrate and a circuit board to which said semiconductor device is electrically connected or a semiconductor chip and a circuit board to which said semiconductor chip is electrically connected further comprising the steps of:
   (b) removing the semiconductor chip or semiconductor device from the circuit board; and
   (c) optionbally, cleaning the surface of the circuit board to remove any cured reaction product that remains.

29. An epoxy- or episulfide-containing aromatic compound within the following formula:

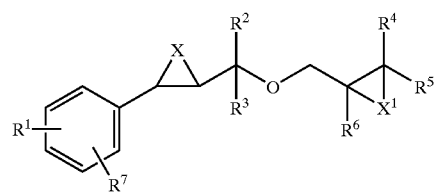

I wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methyl, ethyl, propyl, butyls, phenyl, benzyl, phenoxy, benzyloxy, and when $R^5$ and $R^6$ are present, and taken together, may form a cyclic, bicyclic or heterocyclic structure, which may be substituted by straight chain or branched alkyl groups of from 1 to about 6 carbon atoms, or alkenyl groups of from 2 to about 6 carbon atoms, and X and $X^1$ each are independently selected from oxygen and sulfur.

30. An epoxy-containing aromatic compound within the following formula:

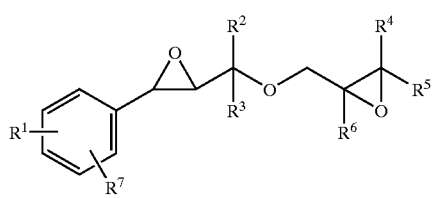

II wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methyl, ethyl, propyl, butyls, phenyl, benzyl, phenoxy, benzyloxy, and when $R^5$ and $R^6$ are present, and taken together, may form a cyclic, bicyclic or heterocyclic structure, which may be substituted by straight chain or branched alkyl groups of from 1 to about 6 carbon atoms, or alkenyl groups of from 2 to about 6 carbon atoms.

31. An episulfide-containing aromatic compound within the following formula:

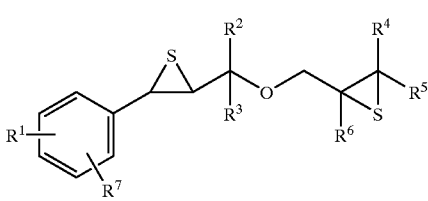

III wherein $R^1$ and $R^7$ each are independently selected from hydrogen, methyl, ethyl, propyl, isopropyl, butyl, isobutyl, tert butyl, $C_{1-4}$ alkoxy, halogen, cyano and nitro, $R^2$ through $R^6$ may or may not be present, but when present are each independently selected from the group consisting of methyl, ethyl, propyl, butyls, phenyl, benzyl, phenoxy, benzyloxy, and when $R^5$ and $R^6$ are present, and taken together, may form a cyclic, bicyclic or heterocyclic structure, which may be substituted by straight chain or branched alkyl groups of from 1 to about 6 carbon atoms, or alkenyl groups of from 2 to about 6 carbon atoms.

* * * * *

UNITED STATES PATENT AND TRADEMARK OFFICE
CERTIFICATE OF CORRECTION

PATENT NO. : 6,572,980 B1
DATED : June 3, 2003
INVENTOR(S) : Klemarczyk et al.

It is certified that error appears in the above-identified patent and that said Letters Patent is hereby corrected as shown below:

Column 12,
Lines 52-53, should read -- ...may be generally represented.. --.

Column 23,
Line 10, should read

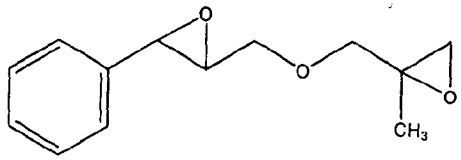

Cinnamyl Oxide Methyl
Propenyl Oxide Ether (COMPOE)

Line 15, should read

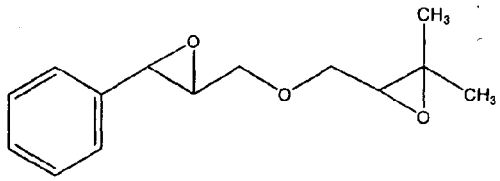

Cinnamyl Oxide Methyl Butene
Oxide Ether (COMPOE)

Signed and Sealed this

Twenty-fourth Day of February, 2004

JON W. DUDAS
*Acting Director of the United States Patent and Trademark Office*